United States Patent [19]

Chandrakumar et al.

[11] Patent Number: 5,661,146

[45] Date of Patent: Aug. 26, 1997

[54] SUBSTITUTED DIBENZOXAZEPINE UREA COMPOUNDS, PHARMACEUTICAL COMPOSITIONS AND METHODS OF USE

[75] Inventors: Nizal Samuel Chandrakumar, Vernon Hills; Donald Willis Hansen, Jr., Skokie; Karen Berenice Peterson, Vernon Hills; Barnett Sylvain Pitzele, Skokie, all of Ill.

[73] Assignee: G.D. Searle & Co., Chicago, Ill.

[21] Appl. No.: 443,506

[22] Filed: May 18, 1995

Related U.S. Application Data

[63] Continuation of Ser. No. 257,841, Jun. 9, 1994, Pat. No. 5,449,675.

[51] Int. Cl.$^6$ .................. A61K 31/35; C07D 267/20; C07D 413/12
[52] U.S. Cl. .................................. 514/211; 540/547
[58] Field of Search .......................... 540/547; 514/211

[56] References Cited

U.S. PATENT DOCUMENTS

| | | | |
|---|---|---|---|
| 2,852,528 | 9/1958 | Hoffmann et al. | 260/327 |
| 3,050,524 | 8/1962 | Yale et al. | 540/547 |
| 3,210,372 | 10/1965 | Werner et al. | 260/309.6 |
| 3,357,998 | 12/1967 | Cusic et al. | 260/333 |
| 3,534,019 | 10/1970 | Coyne et al. | 260/239 |
| 3,565,913 | 2/1971 | Yale et al. | 260/327 |
| 3,624,104 | 11/1971 | Cusic et al. | 260/333 |
| 3,644,346 | 2/1972 | Cusic et al. | 260/240 |
| 3,702,852 | 11/1972 | Yale et al. | 260/327 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244.4 |
| 4,170,593 | 10/1979 | Mueller | 260/243.3 |
| 4,290,953 | 9/1981 | Koizumi et al. | 260/333 |
| 4,379,150 | 4/1983 | Ito et al. | 424/244 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,681,939 | 7/1987 | Mueller | 540/547 |
| 4,704,386 | 11/1987 | Mueller | 514/211 |
| 5,180,720 | 1/1993 | Husa et al. | 514/211 |
| 5,182,272 | 1/1993 | Hallinan et al. | 514/211 |
| 5,212,169 | 5/1993 | Husa et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinan et al. | 514/80 |
| 5,288,719 | 2/1994 | Husa et al. | 514/211 |
| 5,304,644 | 4/1994 | Husa et al. | 540/547 |
| 5,324,722 | 6/1994 | Hagen et al. | 514/211 |
| 5,354,746 | 10/1994 | Chandrakumar et al. | 514/211 |
| 5,354,747 | 10/1994 | Hansen et al. | 514/211 |
| 5,354,863 | 10/1994 | Dappen et al. | 546/35 |
| 5,395,932 | 3/1995 | Chandrakumar et al. | 540/547 |
| 5,449,675 | 9/1995 | Chandrakumar et al. | 514/211 |

FOREIGN PATENT DOCUMENTS

| | | | |
|---|---|---|---|
| 0012385 | 6/1980 | European Pat. Off. | C07D 267/20 |
| 0193822 | 9/1986 | European Pat. Off. | C07D 267/20 |
| 0218077 | 4/1987 | European Pat. Off. | C07D 267/20 |
| 0480641 | 4/1992 | European Pat. Off. | C07D 223/20 |
| 0 512 399 A1 | 11/1992 | European Pat. Off. | C07D 267/20 |
| 0 512 400 A1 | 11/1992 | European Pat. Off. | C07D 413/12 |
| 0534667 | 3/1993 | European Pat. Off. | C07D 417/06 |
| 0 539 977 A1 | 5/1993 | European Pat. Off. | C07D 267/20 |
| 1 318 032 | 1/1963 | France . | |
| 2 130 622 | 11/1972 | France | C07D 87/54 |
| 2 337 130 | 7/1977 | France | C07D 267/20 |
| 6700603 | 7/1967 | Netherlands . | |
| 1170322 | 11/1969 | United Kingdom | C07D 87/54 |
| 1331892 | 9/1973 | United Kingdom | C07D 87/54 |
| 1522003 | 8/1978 | United Kingdom . | |
| WO92/19617 | 11/1992 | WIPO | C07D 413/12 |
| WO93/07132 | 4/1993 | WIPO | C07D 267/20 |
| WO93/09104 | 5/1993 | WIPO | C07D 267/20 |

OTHER PUBLICATIONS

Bennett, et al. "Prostaglandin antagonists.", *Chemical Abstracts*, vol. 76, No. 9, Feb. 28 1972, Abstract No. 42119V.

A. Bennett, et al. "Antagonism of Prostanoid-Induced Contractions of Rat Gastric Fundus Muscle by SC-19220 Sodium Meclofenamate, Indomethacin or Trimethoquinol," *Br. J. Pharmac.*, 71, 169-175 (1980)—London.

W.E. Coyne, et al. "Anticonvulsant Semicarbazides," *J. Med Chem.*, 11(6), 1158-1160 (1968)—USA.

W.E. Coyne, et al. "Antiinflammatory Dialkylaminoalkylureas," *J. Med. Chem.*, 10 (4), 541-46 (1967)—USA.

A.R. Damasio "Alzheimer's Disease and Related Dementias," *Cecil Textbook of Medicine, 19th Ed.*, 2075-2078, (1992).

E.J. Drower, et al. "The Antiociceptive Effects of Prostaglandin Antagonists in the Rat," *European Journal of Pharmacology*, 133, 249-256 (1987)—Europe.

(List continued on next page.)

*Primary Examiner*—Mukund J. Shah
*Assistant Examiner*—Sabiha Qazi
*Attorney, Agent, or Firm*—Fitzpatrick, Cella, Harper & Scinto

[57] ABSTRACT

The present invention provides substituted dibenzoxazepine and dibenzthiazepine compounds of Formula I:

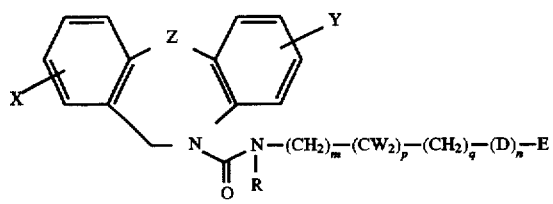

which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

7 Claims, No Drawings

OTHER PUBLICATIONS

F.R. George, et al. "Antagonism of Alcohol Hypnosis by Blockade of Prostaglandin Synthesis and Activity: Genotype and Time Course Effects." *Pharmacology, Biochemistry & Behavior*, vol. 19, 131–136 (1983)—USA.

R. Gimet, et al. "Quantitative Determination of Polymorphic Forms in a Formulation Matrix Using the Near Infra-Red Reflectance Analysis Technique." *Journal of Pharmaceutical & Biomedical Analysis*, vol. 5, No. 3, 205–211 (1987)—Great Britain.

A. Gomes, et al. "Pharmacodynamics of Venom of the Centipede *Scolopendra Subspinipes Dehaani*." *Indian Journal of Experimental Biology*, vol. 20, 615–618, Aug. (1982)—India.

K. Gyires, et al. "Use of the Writhing Test in Mice for Scaling Different Types of Analgesics." *Arch. Int. Pharmacodyn.*, 267, 131–140 (1984)—USA.

D.E. MacIntyre, et al. "Antagonism of Human Platelet Responses to Stimulatory and Inhibitory Prostaglandins." *Prog. Lipid. Res.*, 20 (1–4), 453–9 (1981)—USA.

C.A. Maggi, et al. "The Effect of SC-19220, a Prostaglandin Antagonist, on the Micturition Reflex in Rats." *European Journal of Pharmacology*, 152, 273–279 (1988)—Europe.

K. Nagarajan, et al. "Synthesis of 10,11–Dihydrodibenz[b,f][1,4]oxazepine Derivatives as Potential Anticonvulsant & Psychotropic Agents." *Indian Journal of Chemistry*, vol. 24B, 840–844 (1985)—India.

S. Nakajyo, et al. "Inhibitory Effect of Bassianolide, a Cyclodepsipeptide, on Drug–Induced Contractions of Isolated Smooth Muscle Preparations." *Japan J. Pharmacol.*, 32, 55–64 (1982)—Japan.

A. Rakovska, et al. "Antagonistic Effect of SC-19220 on the Responses of Guinea–Pig Gastric Muscles to Prostaglandins $E_1$, $E_2$, and $F_{2a}$." *Arch. Int. Pharmacodyn.*, 268, 59–69 (1984)—USA.

J.H. Sanner "Dibenzoxazepine Hydrazides as Prostaglandin Antagonists." *Intra–Science Chem. Rept.*, vol. 6, No. 1, 1–9 (1972)—USA.

J.H. Sanner, et al. "Structure–Activity Relationship of Some Dibenzoxazepine Derivatives as Prostaglandin Antagonists." *Advances in the Biosciences*, 9, 139–148 (1972)—USA.

U.S. application No. 07/813,316, Hagen et al., filed Dec. 20, 1991.

U.S. application No. 08/126,826, Husa et al., filed Sep. 24, 1993.

U.S. application No. 08/133,681, Chandrakumar et al., filed Oct. 7, 1993.

U.S. application No. 08/134,345, Chandrakumar et al., filed Oct. 7, 1993.

U.S. application No. 08/147,356, Chrusciel et al., filed Nov. 3, 1993.

SUBSTITUTED DIBENZOXAZEPINE UREA COMPOUNDS, PHARMACEUTICAL COMPOSITIONS AND METHODS OF USE

This Application is a continuation Application of application Ser. No. 08/257,841, filed on Jun. 9, 1994 U.S. Pat. No. 5,449,675.

BACKGROUND OF THE INVENTION

(1) Field of the Invention

The present invention generally relates to compounds having pharmacological activity which are useful as pharmacological agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. No. 3,357,998 discloses derivatives of dihydrodibenz[b,f][1,4]oxazepine-10-carboxylic acids.

U.S. Pat. No. 5,212,169 discloses a class of substituted dibenzoxazepine compounds in which the 2-, 3- and/or 8-position, and/or the side chain, is substituted.

U.S. Pat. No. 5,182,272 discloses 8-substituted-dibenz[b,f][1,4]oxazepine-10(11)-carboxylic acid, substituted hydrazides, pharmaceutical compositions and methods for treating pain.

U.S. Pat. No. 4,681,939 discloses 8-chlorodibenz[b,f][1,4]oxazepine-10-(11H)-carboxylic acid, 2-[(phenylthio)alkanoyl]hydrazides.

U.S. Pat. No. 4,704,386 discloses 8-chlorodibenz[b,f][1,4]oxazepine-10(11)-carboxylic acid, 2-[(phenylsulfinyl and phenylsulfonyl)alkanoylhydrazides.

U.S. Pat. No. 3,644,346 discloses semicarbazones of dibenzoxazepine-N-carboxylic acid hydrazides.

U.S. Pat. No. 4,170,593 discloses 1-(substituted amino) alkanoyl-2-(dibenzoxazepine-10-carbonyl)hydrazines and derivatives thereof.

U.S. Pat. Nos. 4,559,336 and 4,614,617 (a continuation-in-part of U.S. Pat. No. 4,559,336) disclose 8-chlorodibenz[b,f][1,4]oxazepine-10(11H)-carboxylic acid, 2-(sulfinyl- and sulfonyl-containing acyl)hydrazides, and intermediates thereof.

U.S. Pat. No. 3,534,019 discloses hydrazides of dibenzoxazepine-, dibenzothiazepine- and dibenzodiazepine-carboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazine compounds.

U.S. Pat. Nos. 4,045,442, 4,125,532 (a divisional of U.S. Pat. No. 4,045,442) and U.S. Pat. No. 4,170,593 (a divisional of U.S. Pat. No. 4,125,532) disclose 1-(substituted amino)alkanoyl-2-(dibenzoxazepine-10-carbonyl)hydrazine compounds.

PCT/US92/03028 discloses a class of substituted dibenzoxazepine compounds in which-the 2-, 5- and/or 8-position, and/or the side chain, is substituted.

GB 1 522 003 discloses 1-acyl-2-(8-chloro-10,11-dihydrodibenz[b,f][1,4]oxazepine-10-carbonyl)hydrazine compounds.

GB 1 331 892 discloses derivatives of dibenzoxazepine N-carboxylic acid hydrazides.

W. E. Coyne et al., "Anticonvulsant Semicarbazides," *J. Med. Chem.*, 11(6), 1158–1160 (1968), disclose the investigation of the structure-activity relationship of the anticonvulsant activity of a series of semicarbazides which was synthesized from various tricyclic amines (see Table I, Page 1160).

Each of the documents described hereinabove discloses compounds which are structurally different from the compounds of the present invention. Thus, the compounds of the present invention are structurally distinct from that which has been described in the art.

Compounds of the present invention have been found to exhibit activity as prostaglandin $E_2$ antagonists.

SUMMARY OF THE INVENTION

The present invention provides compounds having a structure of Formula I:

Formula I $$\text{X} - \underset{\text{O}}{\underset{\|}{\text{C}}} \cdots \text{N} - \underset{\text{R}}{\text{N}} - (CH_2)_m - (CW_2)_p - (CH_2)_q - (D)_n - E$$

or a pharmaceutically-acceptable salt thereof, wherein:

X is hydrogen, halogen or alkyl;
Y is hydrogen, halogen or alkyl;
Z is oxygen, sulfur, $$\underset{\|}{\underset{\text{O}}{-\text{S}-}} \quad \text{or} \quad \underset{\underset{\text{O}}{\|}}{\overset{\overset{\text{O}}{\|}}{-\text{S}-}};$$

R is hydrogen or alkyl;
W is hydrogen or alkyl;

D is aryl,

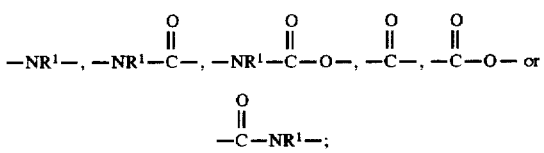

R¹ is hydrogen, alkyl, hydroxy or alkoxy;
E is hydrogen, alkyl, aryl, alkylaryl, —NRR or -alkylene-NRR;
m is an integer of from 0 to 8;
p is 0 or 1;
q is an integer of from 0 to 8; and
n is 0 or 1;
with the proviso that
  (1) n is not 0 when X is hydrogen, Z is oxygen, Y is halogen, R is hydrogen or alkyl and E is —NRR or -alkylene-NRR;
  (2) E is not hydrogen or alkyl when either:
    (a) Z is oxygen, R¹ is hydrogen or alkyl and n is 0; or
    (b) Z is oxygen, R¹ is hydrogen or alkyl, m and p are each 0, n is 1 and D is

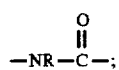

(3) E is not aryl, alkylaryl, —NRR or -alkylene-NRR when either:
    (a) Z is oxygen, R¹ is hydrogen or alkyl, W is hydrogen, p and n are each 1 and D is

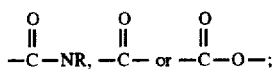

(b) R¹ is hydrogen or alkyl, m and p are each 0, n is 1 and D is

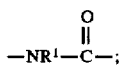

(4) E is not aryl or alkylaryl when X is hydrogen or alkyl, Z is oxygen or sulfur, R¹ is hydrogen or alkyl, m and p are each 0, n is 1 and D is —NR¹—; and
  (5) E is not —NRR or -alkylene-NRR when Z is oxygen or sulfur and m, p and n are each 0.

The present invention also provides pharmaceutical compositions which are pharmaceutically acceptable, and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The term "alkoxy" as used herein means an alkyl radical, as defined below, having an oxygen atom attached thereto. Representative alkoxy groups include methoxy, ethoxy, propoxy, tert-butoxy and the like.

The term "alkyl" as used herein means a saturated hydrocarbon radical having from one to ten carbon atoms, and within which includes from one to six carbon atoms, and further within which includes one, two, three or four carbon atoms, which can be a straight or branched chain. Representative of such radicals are methyl, ethyl, propyl, isopropyl, butyl, sec-butyl, isobutyl, tert-butyl, pentyl and the like.

The term "alkylaryl" as used herein means an alkylene group, as defined below, which has an aryl group, as defined below, attached thereto.

The term "alkylene" as used herein means a straight or branched saturated hydrocarbon chain spacer arm which has from one to ten carbon atoms, and within which includes from one to six carbon atoms, and further within which includes one, two, three or four carbon atoms.

The term "analgesia" as used herein means the reduction, or absence, of sensibility to pain, designating particularly the relief of pain without loss of consciousness.

The term "animal" as used herein includes mammals and nonmammals, and further includes humans and non-human mammals.

The term "aryl" as used herein means 5- or 6-membered single-ring aromatic radicals which may include zero, one, two, three or four heteroatoms selected from nitrogen, sulfur and oxygen, within which includes from zero to two heteroatoms, and further within which includes from zero to one heteroatom. The aryl groups may be present either in the center (i.e., not at an end), or at an end, of the structure of a compound of the present invention. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The abbreviation "Bu" as used herein means butyl (—CH₂CH₂CH₂CH₃).

The abbreviation "CH₃CN" as used herein means acetonitrile.

The abbreviation "CHCl₃" as used herein means chloroform.

The term "composition" as used herein means a product which results from the combining of more than one ingredient.

The abbreviation "DMF" as used herein means dimethylformamide.

The abbreviation "DMSO" as used herein means dimethyl sulfoxide.

The abbreviation "DSC" as used herein means Differential Scanning Calorimetry.

The phrase "EC₅₀ concentration" as used herein means that concentration of a compound or drug which is necessary to elicit a 50% maximal biological response and, thus, which is necessary to elicit a 50% reduction in the contractions of guinea pig ileum segments in a prostaglandin antagonism assay.

The phrase "ED₅₀ dose" as used herein means that dose of a compound or drug which produced a biological effect, such as producing analgesia, in 50% of the animals to which the compound or drug was administered.

The abbreviation "Et" as used herein means ethyl (—CH$_2$CH$_3$).

The abbreviation "Et$_2$O" as used herein means diethyl ether.

The abbreviation "Et$_3$N" as used herein means triethylamine.

The abbreviation "EtOAc" as used herein means ethyl acetate.

The abbreviation "EtOH" as used herein means ethanol (CH$_3$CH$_2$OH).

The term "halogen" as used herein means chlorine (Cl), bromine (Br), fluorine (F) and/or iodine (I).

The term "heteroatom" as used herein means an atom of any element other than carbon or hydrogen.

The abbreviation "HOAc" as used herein means acetic acid.

The abbreviation "HPLC" as used herein means High Pressure Liquid Chromatography.

The term "hydroxy" as used herein means the group —OH.

The abbreviation "IBCF" as used herein means isobutylchloroformate.

The term "intragastrically" and/or the abbreviation "i.g." as used herein means that a compound or drug was administered into the stomach.

The abbreviation "KCN" as used herein means potassium cyanide.

The abbreviation "LiAl H$_4$" as used herein means lithium aluminum hydroxide.

The abbreviation "Me" as used herein means methyl (—CH$_3$).

The abbreviation "MeOH" as used herein means methanol (CH$_3$OH).

The abbreviation "MPLC" as used herein, means Medium Pressure Liquid Chromatography.

The abbreviation "n-BuOH" as used herein means n-butanol (CH$_3$CH$_2$CH$_2$CH$_2$OH).

The abbreviation "(nBu)$_3$SnCl" as used herein means tri n-butyltin chloride.

The phrase "N-protecting group" or "N-protected" as used herein means those groups intended to protect the N-terminus of an amino acid or peptide, to protect an amino group against undesirable reactions during synthetic procedures and includes, but is not limited to, aryl, sulfonyl, acyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "NAN$_3$" as used herein means sodium azide.

The abbreviation "NMM" as used herein means N-methylmorpholine.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts and alkali metal salts such as sodium and potassium and alkaline earth salts, such as calcium and magnesium.

The term "phenyl," and the abbreviation "Ph," as used herein means the group C$_6$H$_5$—, derived from benzene.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The abbreviation "s.c." as used herein means that a compound or drug was administered subcutaneously.

The abbreviation "SOCl$_2$" as used herein means thionylchloride.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product," "title material" and "title salt" as used herein mean that compound, product, material or salt whose chemical name is given, and/or whose structure is shown, in the particular example, or subpart thereof, referred to. If no particular example, or subpart thereof, is referred to, it means that compound, product, material or salt whose chemical name is given, and/or whose structure is shown, in the particular example, or subpart thereof, in which it appears.

The letters "L" and "D" appearing herein indicate whether a particular compound has the S configuration (L) or the R configuration (D) by amino acid definitions, as known by those of skill in the art.

The "*" symbol as used herein indicates a chiral (assymetric) center in the chemical structure of the compound in which it appears.

(2) Description of Invention

In one aspect, the present invention provides compounds comprising a structure of Formula I, as described above, and pharmaceutically-acceptable salts thereof.

The compounds of the present invention comprise a class of substituted dibenzoxazepine compounds in which the 1-, 2-, 3-, 4-, 5-, 6-, 7-, 8-, 9-, and/or 10-position, is substituted. Such compounds have been shown to exhibit activity as prostaglandin $E_2$ antagonists.

Specific compounds within the scope of the invention include, but are not limited to, the compounds discussed in the examples presented below, as well as the pharmaceutically-acceptable salts thereof.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate and lactobionate salts and the like. (See, for example, S. M. Berge et al., "Pharmaceutical Salts," *J. Pharm. Sci.*, 66:1–19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, and methods for treating central nervous disorders, including convulsions and ischemia, as well as asthma, enuresis, arrhythmia, diarrhea, dysmenorrhea, osteoporosis, urinary incontinence, gastric hypermotility and irritable bowel syndrome in an animal, comprising administering a therapeutically-effective amount of a compound of Formula I, as described hereinabove, to the animal.

The most preferred embodiment of the present invention is the compound described in Example 32 below.

(3) Utility

Compounds of the present invention exhibit activity as prostaglandin $E_2$ antagonists of (prostaglandin antagonists of the $E_2$ series) and, thus, are useful for treating diseases responsive to prostaglandin-$E_2$ antagonists in an animal.

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia, diarrhea, urinary incontinence, gastric hypermotility and irritable bowel syndrome by virtue of their activity as prostaglandin $E_2$ antagonists. They would also be useful as antipyretic agents by virtue of this activity.

(4) Methods of Preparation

In general, the compounds of the present invention may be prepared by the methods illustrated in the following general reaction scheme, or by modifications thereof, using readily-available starting materials, reagents and conventional synthesis procedures. Unless otherwise specified, the various substituents of the compounds and materials present in the general reaction scheme are defined in the same manner as they are defined above in Formula I.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In the General Reaction Scheme presented hereinbelow, the Z variable may be oxygen, sulfur, —SO— or —SO$_2$—. Where Z is sulfur, oxidation of the sulfur may be achieved with hydrogen peroxide to have Z become —SO—. Oxidation of the —SO— group may then be achieved with hydrogen peroxide to have Z become —SO$_2$—.

In the General Reaction Scheme, X may be hydrogen, halogen or alkyl, Y may be hydrogen, halogen or alkyl, Z may be oxygen, sulfur,

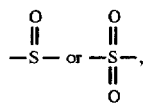

R may be hydrogen or alkyl, W may be hydrogen or alkyl, D may be aryl,

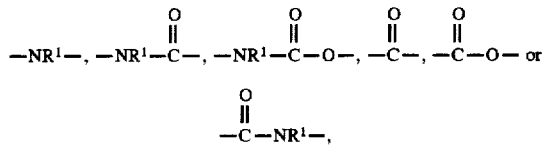

R$^1$ may be hydrogen, alkyl, hydroxy or alkoxy, E may be hydrogen, alkyl, aryl, alkylaryl, —NRR or -alkylene-NRR, m may be an integer of from 0 to 8, p may be 0 or 1, q may be an integer of from 0 to 8 and n may be 0 or 1.

In the General Reaction Scheme, phenols or thiophenols are converted to their sodium salts with sodium hydride. The resulting salts are condensed with an ortho-chloro nitrobenzene to generate diaryl ethers or thioethers. Catalytic hydrogenation of these intermediates sequentially reduces the nitro function to the amine, which then undergoes cyclization via imine formation. The imine, under the hydrogenation conditions, is subsequently reduced generating the dibenzoxazepines or dibenzthiazepines. These tricycles are then converted to their carbonyl chloride derivatives and these intermediates are condensed with a functionalized primary or secondary amine to yield either the final products, the free bases of the final products or intermediates containing an alterable functional group, (D)$_n$-E. These intermediates containing a (D)$_n$-E function are transformed to final products or the free bases of final products. In syntheses by either of these methods, the free bases are converted to their HCl salts with HCl in dioxane. The dibenzthiazepine compounds are oxidized to their sulfoxides by treatment with 30% hydrogen peroxide at room temperature, and to their sulfones by treatment with 30% hydrogen peroxide at 50° C.

GENERAL REACTION SCHEME

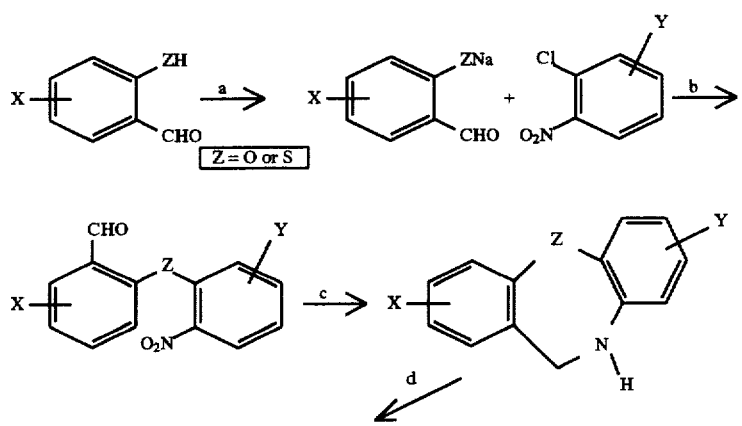

-continued
GENERAL REACTION SCHEME

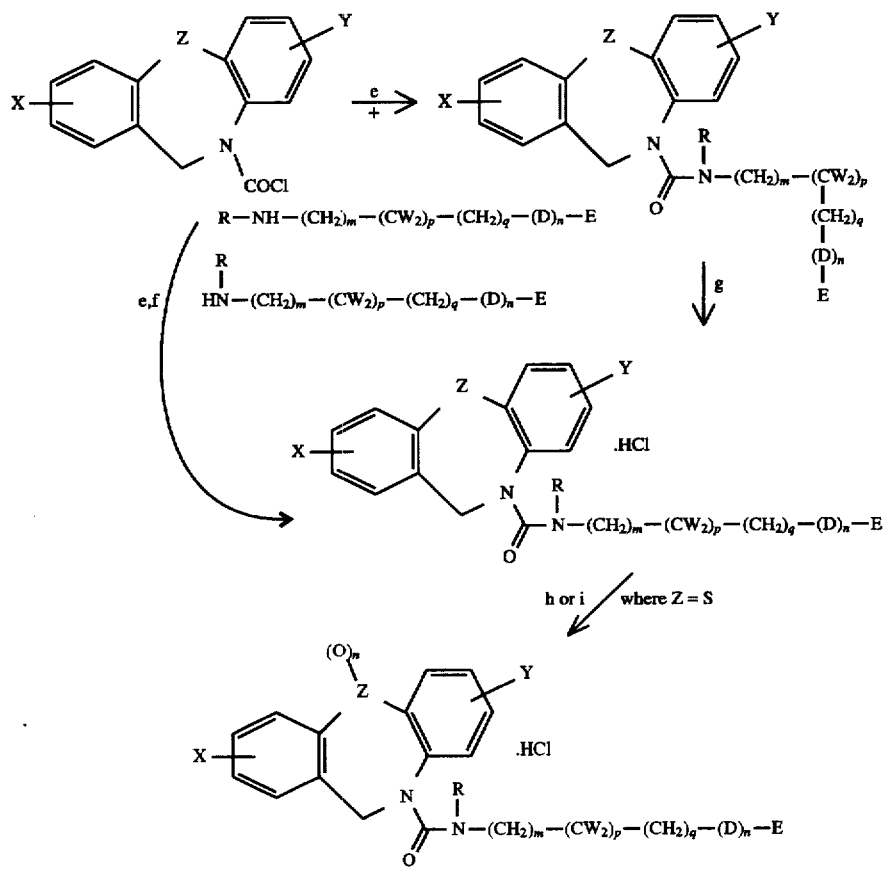

a) sodium hydride (NaH), DMF. b) heat. c) hydrogen, Raney nickel catalyst. d) phosgene in toluene or carbonyldiimidazole in THF. e) Et$_3$N, Molecular Sieves in CH$_2$Cl$_2$. f) 6N HCl/dioxane, Et$_2$O or MeOH and water. g) where E = H; hydrogen, Pd on C catalyst or mixed anhydride coupling. h) n = 1; 30% H$_2$O$_2$, acetic acid, room temperature. i) n = 2; 30% H$_2$O$_2$, acetic acid, 50° C.

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a particular patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or salt thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to;alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the present invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound (a compound of Formula I) per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods for preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile, injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically-acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the present invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable media just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention., and the pharmaceutical compositions comprising such compounds.

In the examples, all parts are by weight unless otherwise indicated.

All equipment employed in the examples is commercially available.

Unless otherwise indicated in a particular example, all starting materials employed in the examples are commercially available. Sources for these starting materials and pieces of equipment include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), Chemical Dynamics Corp. (South Plainfield, N.J.) and Pfaltz & Bauer (Waterbury, Conn.). Most of the starting materials were obtained from Aldrich Chemical Co. (Milwaukee, Wis.). The synthesis procedures for any starting materials employed in the examples which are not commercially available are described in the examples.

All patents and publications referred to in the examples, and throughout the specification, are hereby incorporated herein by reference, without admission that such is prior art.

EXAMPLE 1

8-chloro-10,11-dihydrodibenz[b,f][1,4]oxazeptne (1)

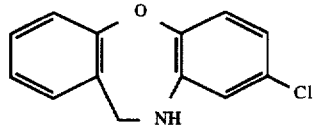

The synthesis of the title compound is described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether ($Et_2O$). The ether layer was filtered to remove insoluble material, and the resultant solution was dried over sodium sulfate ($Na_2SO_4$). The ether solvent was evaporated, and the residual oil was recrystallized from a mixture of hexane and benzene to give 2-(2-nitro-4-chlorophenoxy) benzaldehyde melting at about 100°–101° C.

A solution of 55 parts of the ether obtained in the preceding paragraph in 800 parts of ethanol (EtOH) was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered and cooled. There was obtained yellowish-white crystals which were separated by filtration to give the title compound melting at about 94°–95° C.

EXAMPLE 2

8-chlorodibenz[b,f][1,4]oxazepin-10(11H)-carbonyl chloride (2)

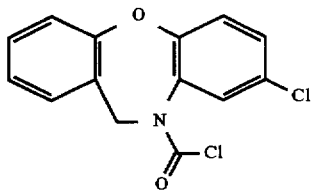

The title compound was also synthesized in the manner described in U.S. Pat. No. 3,534,019.

Briefly, 13 parts of phosgene in 45 parts of toluene was stirred for 2 hours at 5°–10° C., and then 70 parts of ether was added. This was followed by the addition of a solution of 18.9 parts of the title compound of Example 1 and 7.2 parts of triethylamine in 140 parts of ether. After the addition was complete, the mixture was stirred for 2 hours, and then was filtered. The solvent was then evaporated from the filtrate. The resultingresidue was then dissolved in 200 parts by volume of hot hexane, and this mixture was then filtered and cooled to provide the title compound, mp=100°–102° C.

EXAMPLE 3 ethyl 2-[[(8-chlorodibenz[b.f][1.4]oxazepine-10 (11H)-yl)carbonyl]amino]acetate (3)

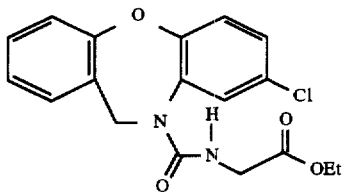

To the product of Example 1 (5.0 g, 21.6 mmol) in 50 mL of toluene was added ethyl isocyanatoacetate (4.2 g, 32.4 mmol). This mixture was then brought to reflux and maintained under nitrogen ($N_2$) for 17 hours. After cooling the reaction to room temperature, all solvent was removed under reduced pressure. The residue was taken up in $Et_2O$ and washed with 1N NaOH, water, 1N hydrochloric acid (HCl), and saturated aqueous sodium chloride (brine). The solution was then dried ($Na_2SO_4$) and all solvent was removed under reduced pressure. The crude product was flash chromatographed on silica gel eluting with 40% ethyl acetate (EtOAc) /n-hexane to yield 5.4 g of the title product.

EXAMPLE 4

2-[[(8-chlorodibenz[b.f][1.4]oxazepin-10(11H)-yl) carbonyl]amino]acetic acid (4)

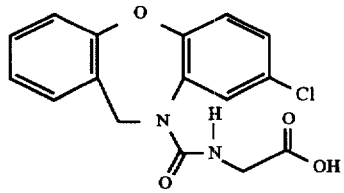

To the product of Example 3 (5.1 g, 14.2 mmol) dissolved in 100 mL of methanol (MeOH) was added 25 mL (25.0 mmol) of 1N sodium hydroxide. (NaOH). This reaction was stirred at room temperature overnight before all solvent was removed under reduced pressure. The residue was dissolved in 250 mL of water and the solution was brought to pH 3 with 1N HCl. The product was extracted from the aqueous phase with 3×250 mL of $Et_2O$. The $Et_2O$ layer was then dried ($Na_2SO_4$), filtered, and stripped of all solvent under reduced pressure to provide 4.7 g of the title compound after drying in a vacuum oven.

EXAMPLE 5

8-chloro-N-[[[(4-pyridylmethyl)-amino]carbonyl] methyl]-10(11H)-dibenz[b.f][1.4] oxazepinecarboxamide (5)

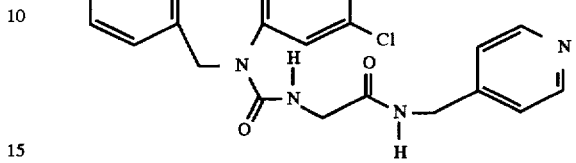

To the title compound of Example 4 (0.5 g, 1.5 mmol) in 20 mL of methylene chloride ($CH_2Cl_2$) was added N-methylmorpholine (NMM, 0.16 mL, 1.5 mmol). After cooling this solution to about −70° C., isobutylchloroformate (IBCF, 0.2 mL, 1.5 mmol) was added and the reaction was warmed to 0° C. and maintained at this temperature for 45 minutes. The reaction was then recooled to about −70° C. and treated with 4-(aminomethyl)pyridine (0.15 mL, 1.5 mmol) before allowing it to warm to room temperature. The precipitated white solid was filtered from the reaction mixture, which was partitioned between 1N NaOH and EtOAc, filtered, washed with brine, and dried to yield 200 mg of the title material.

Analysis Calculated for $C_{22}H_{19}N_4O_3Cl+0.1\ H_2O$ (MW=424.68): C, 62.22; H, 4.56; N, 13.19; Cl, 8.35. Found: C, 61.88; H, 4.50; N, 13.11; Cl, 8.78.

EXAMPLE 6

8-chloro-N-[[[(4-pyridinylmethyl)amino]-carbonyl] methyl]-10(11H)-dibenz[b.f][1.4]-oxazepinecarboxamide, hydrochloride (6)

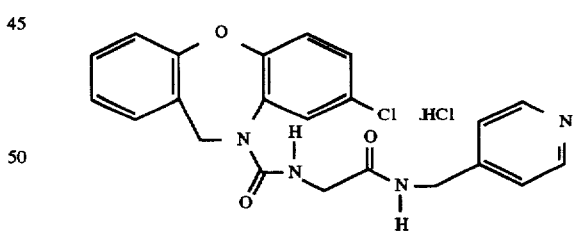

To the title compound of Example 5 (0.10 g, 0.23 mmol) suspended in 30 mL of water was added 0.5 mL of 1N HCl. After stirring this suspension overnight at room temperature, 15 mL of MeOH were added giving a homogeneous solution. This reaction was diluted to 100 mL with water and lyophilized to provide 92 mg of the title compound as a white solid salt.

Analysis Calculated for $C_{22}H_{19}N_4O_3Cl+1.2\ H_2O$ (MW=488.24): C, 54.12; H, 4.65; N, 11.48; Cl, 15.97. Found: C, 54.14; H, 4.47; N, 11.21; Cl, 15.85.

EXAMPLE 7

8-chloro-N-[[[[2-(2-pyridinyl)ethyl]amino]-carbonyl]methyl]-10(11H)dibenz[b,f][1,4]-oxazepinecarboxamide (7)

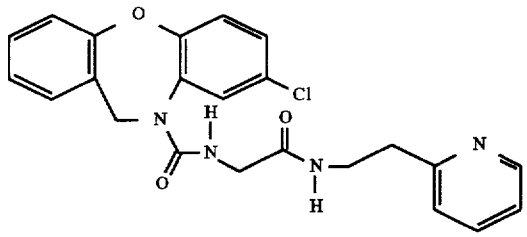

By the method described in Example 5, the title compound of Example 4 (0.5 g, 1.5 mmol) in 20 mL of CH₂CL₂ was converted to its mixed anhydride with NMM (0.16 mL, 1.5 mmol) and IBCF (0.2 mL, 1.5 mmol) and coupled to 2-(2-aminoethyl)pyridine (0.18 mL, 1.5 mmol). This procedure gave 362 mg of the title compound after Chromatotron® chromatography eluting with 5% ethanol (EtOH)/CH₂CL₂ containing 1% ammonium hydroxide (NH₄OH).

Analysis Calculated for $C_{23}H_{21}N_4O_3Cl+0.2\ H_2O$ (MW= 440.50): C, 62.71; H, 4.90; N, 12.70; Cl, 8.05. Found: C, 62.51; H, 4.89; N, 12.41; Cl, 8.36.

EXAMPLE 8

8-chloro-N-[[[[2-(2-pyridinyl)ethyl]amino]-carbonyl|methyl]-10(11H)dibenz[b,f][1,4]-oxazepinecarboxamide hydrochloride (8)

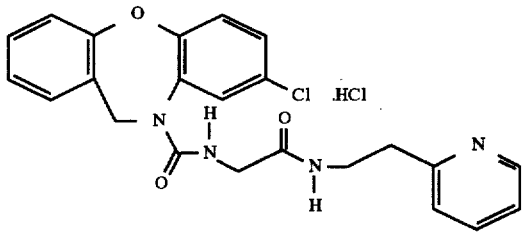

The title compound of Example. 7 (0.1 g, 0.23 mmol) was converted to the present title compound (50 mg) by the method described in Example 6.

Analysis Calculated for $C_{23}H_{21}N_4O_3Cl+1.2\ HCl+0.9\ H_2O$ (MW=496.87): C, 55.60; H, 4.87; N, 11.28; Cl, 15.70. Found: C, 55.80; H, 4.59; N, 11.26; Cl, 15.46.

EXAMPLE 9

3-(4-pyridinyl)propyl 8-chloro-10(11H)dibenz[b,f][1,4]oxazepinecarboxylate (9)

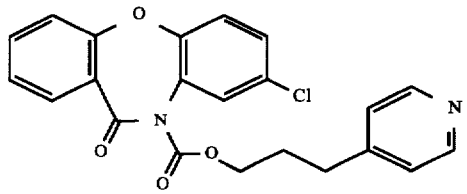

A tetrahydrofuran (THF, 25 mL) solution of 3-(4-pyridyl)-1-propanol (470 mg, 3.4 mmol) was cooled to 0° C. under a N₂ atmosphere before a 60%-mineral oil dispersion of sodium hydride (NaH, 136 mg, 3.4 mmol) was added. After 30 minutes, the title compound of Example 2 (1.0 g, 3.4 mmol) was added to the reaction and the mixture was allowed to warm to room temperature and stirred an additional 15 hours. The reaction was again cooled to 0° C. and another 164 mg of NaH was added. After it was warmed to room temperature and stirred for another 15 hours, the reaction was poured into a mixture of 5% NaHCO₃ (100 mL) and EtOAc (200 mL). The aqueous phase was separated and discarded. The organic phase was washed with 2×75 mL of brine, dried (Na₂SO₄), filtered and stripped of all solvent under reduced pressure. The residue was purified by high performance liquid chromatography (HPLC) on silica gel to yield 490 mg of the light orange viscous oil title product.

Analysis Calculated for $C_{22}H_{19}N_2O_3Cl+0.3\ CH_2Cl_2$ (MW=420.34): C, 63.72; H, 4.70; N, 6.66; Cl, 13.50. Found: C, 63.90; H, 4.40; N, 6.55; Cl, 13.23.

EXAMPLE 10

3-(4-pyridinyl)propyl 8-chloro-10(11H)dibenz[b,f][1,4]oxazepinecarboxylate, monohydrochloride (10)

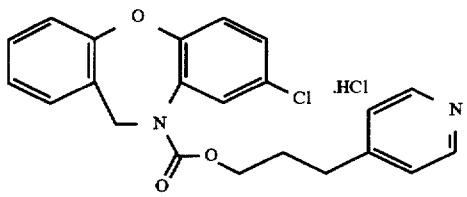

The title product of Example 9 (419 mg, 1.0 mmol) dissolved in 60 mL of Et2O was treated dropwise with 6.9 N HCl/dioxane until no further precipitation of product was noted. The white solid was then filtered, washed with Et₂O, and dried in vacuo to yield 426 mg of the title salt.

Analysis Calculated for $C_{22}H_{19}N_2O_3Cl+HCl$ (MW= 431.32): C, 61.26; H, 4.67; N, 6.50; Cl, 16.44. Found: C, 61.10; H, 4.79; N, 6.34; Cl, 16.15.

EXAMPLE 11

[2-(dimethylaminomethyl)furan-5-yl]methyl-8-chlorodibenz[b,f][1,4]oxazepine-10(11H)-carboxylate (11)

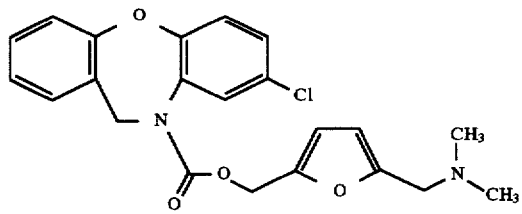

To 2-(dimethylaminomethyl)-4-hydroxymethylfuran (0.53 g, 3.40 mmol) in 30 mL of THF cooled to −78° C. was added dropwise (5 minutes) a solution of 1.6M n-butyllithium in hexane (2.2 mL, 3.40 mmol) to generate the lithium salt. The reaction was stirred at −78° C. for 30 minutes, warmed slowly to −20° C., and recooled to −78° C. before the title compound of Example 2 (1.0 g, 3.40 mmol) was added. The reaction was warmed to room temperature and stirred for 48 hours. The mixture was partitioned between EtOAc and 1M $K_2CO_3$. The organic fraction was washed with 2×100 mL of brine, dried ($Na_2SO_4$), filtered and stripped of all solvent under reduced pressure. The residue was purified by HPLC on silica gel to yield the title compound (1.04 g) as pale yellow oil.

Analysis Calculated for $C_{22}H_{21}N_2O_4Cl+0.05\ CH_2Cl_2$ (MW=417.12): C, 63.49; H, 5.10; N, 6.72; Cl, 9.35. Found: C, 63.42; H, 5.15; N, 6.69; Cl, 9.16.

EXAMPLE 12

2-(dimethylaminomethyl)furan-5-yl]methyl-8-chlorodibenz[b,f][1,4]oxazepine-10(11H)-carboxylate, monohydrochloride (12)

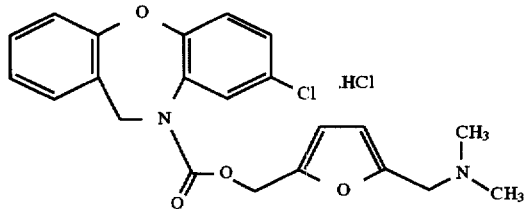

The title product of Example 11 (714 mg, 1.73 mmol) dissolved in 50 mL of $Et_2O$ and 2 mL of MeOH was treated dropwise with 6.9N HCl/dioxane until no further precipitation of solid was noted. All solvent was removed from the mixture under reduced pressure and the residue was triturated with $Et_2O$ to produce the white solid product. This material was filtered, washed with $Et_2O$, and dried in vacuo to give 834 mg of the title salt.

Analysis Calculated for $C_{22}H_{21}N_2O_4Cl+HCl+0.5\ H_2O$ (MW=458.39): C, 57.65; H, 5.06; N, 6.11; Cl, 15.47. Found: C, 57.31; H, 5.07; N, 5.93; Cl, 15.88.

EXAMPLE 13

3-[[4-pyridinyl)methyl]amino]propyl-8-chlorodibenz[b,f][1,4]oxazepine-10(11H)-carboxylate (13)

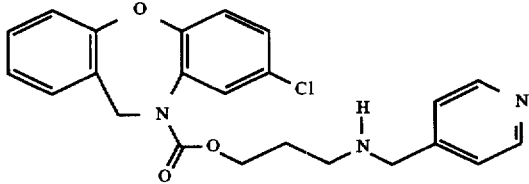

By the procedure described in Example 11, 3-(4-pyridylmethylamino)-1-propanol (1.0 g, 3.4 mmol) in 30 mL of THF was converted to its lithium salt with 1.6M n-butyllithium in hexane (2.1 mL, 3.4 mmol) and reacted with the product of Example 2 (1.0 g, 3.4 mmol) to yield 590 mg of the title product.

Analysis Calculated for $C_{22}H_{22}N_3O_3Cl+0.13\ CH_2Cl_2+0.25\ H_2O$ (MW=439.44): C, 63.22; H, 5.22; N, 9.56; Cl, 10.17. Found: C, 63.14; H, 5.18; N, 9.54; Cl, 10.00.

EXAMPLE 14

3-[[(4-pyridinyl)methyl]amino]propyl-8-chlorodibenz[b,f][1,4]oxazepine-10(11H)-carboxylate, hydrochloride (14)

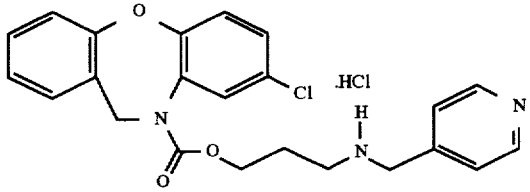

By the method described Example 18, the product of Example 13 (480 mg, 1.09 mmol) in 50 mL of $Et_2O$ was treated with 6.9N HCl/dioxane to generate 513 mg of the title material.

Analysis Calculated for $C_{23}H_{21}N_3O_3Cl+1.5\ HCl+0.25\ H_2O$ (MW=483.10): C, 57.18; H, 5.01; N, 8.70; Cl, 18.35. Found: C, 57.01; H, 5.00; N, 8.63; Cl, 18.46.

EXAMPLE 15

8-chloro-N-[[[f4-pyridinyl)amino]carbonyl]-methyl]dibenz[b,f][1,4]oxazepine-10(11H)-carboxamide (15)

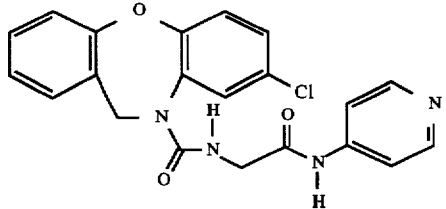

By the method described in Example 5, the title compound of Example 4 (0.5 g, 1.5 mmol) in 20 mL of $CH_2Cl_2$ was converted to its mixed anhydride with NMM (0.16 mL, 1.5 mmol) and IBCF (0.2 mL, 1.5 mmol). This intermediate was condensed with 4-aminopyridine (0.21 g, 2.25 mmol) to produce the title compound (94 mg).

EXAMPLE 16

8-chloro-N-[[[(4-pyridinyl)amino]carbonyl]-methyl]dibenz[b,f][1,4]oxazepine-10(11H)-carboxamide, monohydrochloride (16)

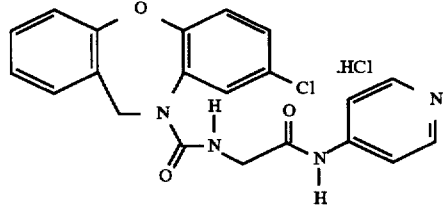

The title compound of Example 15 (90 mg, 0.2 mmol) in 20 mL of MeOH and 1 mL of dimethyl sulfoxide (DMSO) was treated with 3 mL of 2N HCl/MeOH. All solvent was removed under reduced pressure and the residue was lyophilized twice from water to give 26 mg of the title material.

Analysis Calculated for $C_{21}H_{17}N_4O_3Cl+1.0\ HCl+0.6\ H_2O$ (MW=456.11): C, 55.30; H, 4.24; N, 12.28; Cl, 15.55. Found: C, 55.14; H, 4.14; N, 11.77; Cl, 15.29.

EXAMPLE 17 phenylmethyl N-(2-amino-2-methylpropyl) carbamate (17)

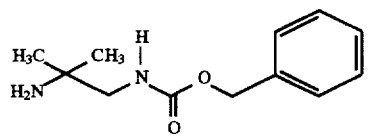

To a 65 g sample of 1,2-diamino-2-methylpropane dissolved in 650 mL of toluene cooled to −5° C. was added dropwise over 45 minutes a toluene solution (200 mL) of benzylchloroformate (52 g, 1.18 mmol). The reaction was warmed to room temperature and stirred for 2 hours before it was filtered and the filtrate was stripped of all solvent under reduced pressure. The residue, dissolved in $CH_2Cl_2$ (100 mL), was filtered and the filtrate again was stripped of all solvent to produce the title compound (54 g) as a viscous oil.

EXAMPLE 18 phenylmethyl N-[2-[[(8-chlorodibenz[b,f][1,4]-oxazepine-10(11H)-yl]carbonyl]amino]-2-methylpropyl]carbamate (18)

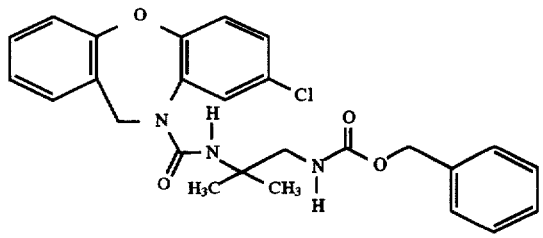

The title compound of Example 2 (5.0 g, 17.0 mmol) in 100 mL of $CH_2Cl_2$ was combined with molecular sieves #5A (5 g), the product of Example 17 (3.8 g, 17.0 mmol), and triethylamine ($Et_3N$, 2.4 mL, 17.2 mmol). After stirring the reaction at room temperature for 17 hours, another 3.1 g of the product of Example 17 was added and stirring was continued for another 17 hours. The reaction was filtered and the filtrate was stripped of all solvent under reduced pressure to yield a white foam solid that was purified by HPLC on silica gel to give 7.4 g of the title material as a white solid.

Analysis Calculated for $C_{26}H_{26}N_3O_4Cl$ (MW=479.97): C, 65.06; H, 5.46; N, 8.75; Cl, 7.39. Found: C, 65.15; H, 5.56; N, 8.64; Cl, 7.20.

EXAMPLE 19

8-chloro-N-(cyanomethyl)dibenz[b,f][1,4]-oxazepin-10(11H)-carboxamide (19)

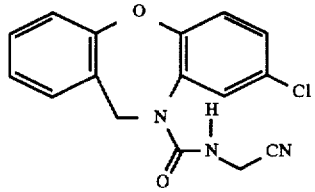

By the method of Example 18, the title compound of Example 2 (5.24 g, 17.8 mmol) in 100 mL of $CH_2Cl_2$ with molecular sieves #5A (10 g) and $Et_3N$ (2.5 mL, 18.0 mmol) was reacted with aminoacetonitrile (1.0 g, 17.8 mmol) to produce 4.5 g of the title product.

EXAMPLE 20

8-chloro-N-[(2H-tetrazol-5-yl)methyl]dibenz[b,f][1,4]oxazepine-10(11H)-carboxamide, sodium salt, hydrate (20).

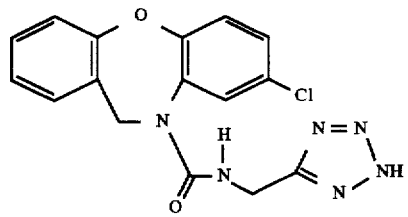

To the product of Example 19 (1.0 g, 3.19 mmol) dissolved in 100 mL of toluene was added sodium azide ($NaN_3$, 0.21 g, 3.19 mmol) and tri n-butyltin chloride ($(nBu)_3SnCl$, 1.14 g, 3.5 mmol). This mixture was refluxed for 7 days before an additional 0.31 mL of $(nBu)_3SnCl$ and 0.1 g of $NaN_3$ were added to the reaction. It was refluxed another 24 hours, cooled to room temperature and treated with 20 mL of 2N HCl. After stirring the mix for 1.25 hours, 20 mL of water were added and the crude product was filtered from the mixture. This material was purified by HPLC on silica gel to yield 360 mg of the title material.

Analysis Calculated for $C_{16}H_{13}N_6O_2Cl$ (MW=356.77): C, 47.78; H, 3.66; N, 20.90; Cl, 8.82. Found: C, 48.03; H, 3.42; N, 20.80; Cl, 9.28.

EXAMPLE 21

4-(3-chloropropyl)pyridine (21)

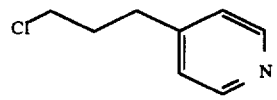

To a stirred solution of 3-(4-pyridyl)propanol (22.05 g, 0.16 mol) in 100 mL of dry chloroform ($CHCl_3$) at 0° C. was added dropwise a $CHCl_3$ solution of thionylchloride ($SOCl_2$, 17.5 mL, 0.24 mol). The reaction was allowed to warm to room temperature, stirred for 1 hour, and then brought to reflux for 1 hour. After cooling the reaction to room temperature, it was stripped of all solvent under reduced pressure and the residue was partitioned between CH₂Cl₂ and water that had been made basic with concentrated NH₄OH. The aqueous phase was washed 2× with CH₂Cl₂ and the combined organic phase was dried (Na₂SO₄), filtered, and stripped of solvent to yield 24 g of crude product. This material was vacuum distilled at 68°–71° C. (0.3 mm) to give 24 g of the title compound.

EXAMPLE 22

4-pyridinebutyronitrile (22)

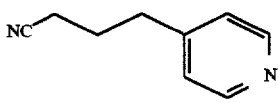

To the product of Example 21 (6.7 g, 42.9 mmol) in 300 mL of acetonitrile (CH₃CN), was added potassium cyanide (KCN, 11.2 g, 171.7 mmol) and dibenzo-18-crown-6 (1.0 g, 2.8 mmol). After the reaction had been refluxed for 18 hours, it was cooled to room temperature, and stripped of all solvent under reduced pressure. The residue was partitioned between 100 mL each of water and CH₂C₂ and the aqueous phase was washed with 3×100 mL of CH₂Cl₂. The combined organic phase was dried (Na₂SO₄), filtered, and stripped of solvent to yield 6.7 g of crude product. This material was purified by HPLC on silica gel to yield 5.3 g of the title material as a yellow oil.

EXAMPLE 23

4-pyridinebutanamine (23)

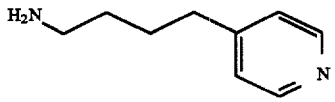

The title product of Example 22 (5.0 g, 34.0 mmol) in 40 mL of tetrahydrofuran was added dropwise to a stirred suspension of lithium aluminum hydride (LiAlH₄, 3.2 g, 85.0 mmol) in 100 mL of THF over 20 minutes. The reaction was brought to reflux for 2 hours, cooled to 10° C., and treated with water (33.2 mL), 15% NaOH (3.2 mL), and then water (9.6 mL) again. The mixture was filtered and the solid was washed With Et₂O. The filtrate was dried (Na₂SO₄), filtered, and stripped of solvent to yield 4.0 g of crude product that was distilled to produce the title compound (340 mg).

EXAMPLE 24

8-chloro-N-[4-(4-pyridinyl)butyl]dibenz[b,f]-[1,4]oxazepine-10(11H)-carboxamide (24)

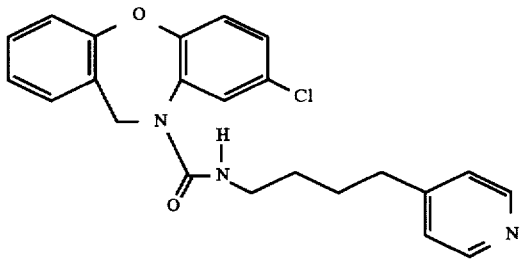

By the method described in Example 18, the title compound of Example 2 (0.98 g, 3.3 mmol) in 30 mL of CH₂Cl₂ with molecular sieves #5A (3 g) and Et₃N (0.47 mL, 3.36 mmol) was reacted with the title compound of Example 23 (0.5 g, 3.3 mmol) to produce 0.82 g of the title product.

EXAMPLE 25

8-chloro-N-[4-(4-pyridinyl)butyl]dibenz[b,f][1,4]oxazepine-10(11H)-carboxamide, hydrochloride (25)

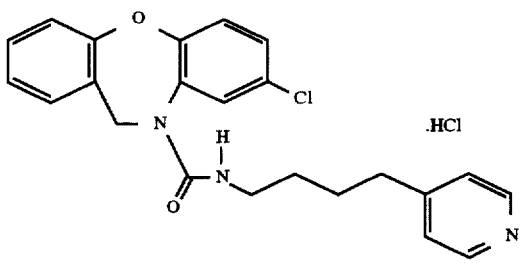

By the method described in Example 16, the title compound of Example 24 (0.82 g, 2.0 mmol) in 40 mL of MeOH was treated with 2N HCl/MeOH (5 mL) to produce 0.25 g of the title product.

Analysis Calculated for C₂₃H₂₂N₃O₂Cl+1.1 HCl+1.5 H₂O (MW=475.03): C, 58.15; H, 5.54; N, 8.85; Cl, 15.67. Found: C, 57.79; H, 5.05; N, 8.54; Cl, 15.82.

EXAMPLE 26

N-(2-amino-1,1-dimethylethyl)-8-chlorodibenz[b,f][1,4]oxazepin-10(11H)-carboxamide (26)

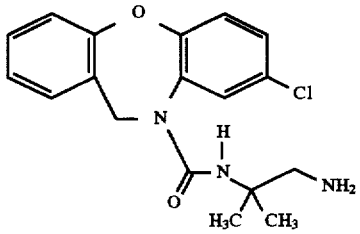

The title product of Example 18 (6.5 g, 13.4 mmol) dissolved in a mixture of EtOH and THF was hydrogenated in a standard Parr apparatus using 3% Pd on carbon as catalyst. The reaction was run under a H₂ pressure of 5 psi for 5.5 hours at 40° C. to produce the crude product. This material was purified by HPLC on silica gel to yield 1.5 g of the title material.

EXAMPLE 27

8-chloro-N-[2-[[(4-pyridinyl)carbonyl]amino-1,1-dimethylethyl]dibenz[b,f][1,4]oxazepine-10(11H) carboxamide (27)

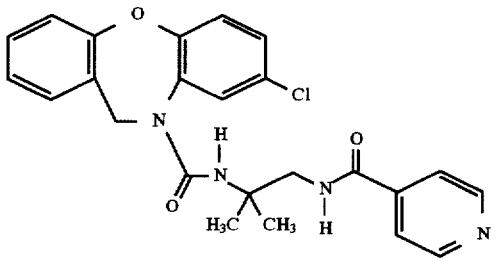

Isonicotinic acid (0.18 g, 1.44 mmol) in 25 mL of $CH_2Cl_2$ was coupled to the product of Example 26 (0.5 g, 1.44 mmol) by the method described in Example 5 using IBCF (0.19 mL, 1.44 mmol) and NMM (0.16 mL, 1.44 mmol). Purification of the crude product by HPLC on silica gel gave 0.41 g of the title compound.

EXAMPLE 28

8-chloro-N-[2-[[(4-pyridinyl)carbonyl]amino-1,1-dimethylethyl]dibenz[b,f][1,4]oxazepine-10(11H) carboxamide, hydrochloride hydrate (28)

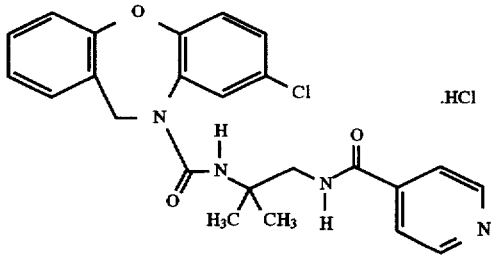

By the method described in Example 16, the title compound of Example 27 (0.38 g, 2.0 mmol) in 40 mL of MeOH was treated with 2N HCl/MeOH (5 mL) to produce 0.25 g of the title product.

Analysis Calculated for $C_{24}H_{23}N_4O_3Cl+0.9$ HCl+1.0 $H_2O$ (MW=501.75): C, 57.45; H, 5.20; N, 11.17; Cl, 13.42. Found: C, 57.47; H, 4.82; N, 11.10; Cl, 13.31.

EXAMPLE 29

5-(diethylamino)pentyl 8-chlorodibenz[b,f]-[1,4] oxazepine-10(11H)-carboxylate (29)

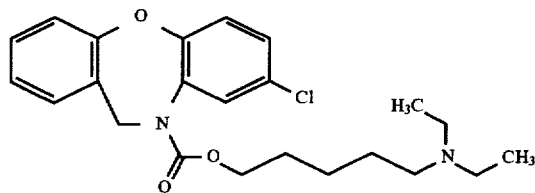

By the procedure described in Example 11, 5-diethylamino-1-pentanol (0.83 g, 5.2 mmol) in 30 mL of THF was converted to its lithium salt with 1.6M n-butyl lithium in hexane (4.3 mL, 5.3 mmol) and reacted with the product of Example 2 (1.5 g, 5.1 mmol) to yield 1.1 g of the title product.

Analysis Calculated for $C_{23}H_{29}N_2O_3Cl+0.5$ $H_2O$ (MW= 419.20): C, 65.90; H, 7.03; N, 6.68; Cl, 8.46. Found: C, 65.98; H, 7.11; N, 6.60; Cl, 8.30.

EXAMPLE 30

5-(diethylamino)pentyl 8-chlorodibenz[b,f][1,4]-oxazepine-10(11H) -carboxylate, monohydrochloride (30)

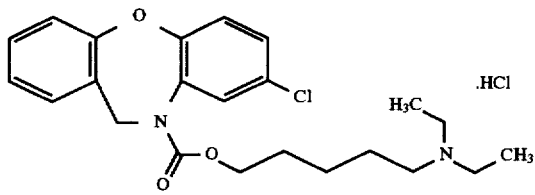

By the method described in Example 10, the product of Example 29 (1.1 g, 2.4 mmol) in 50 mL of $Et_2O$ was treated with 6.9N HCl/dioxane to generate 654 mg of the title material.

Analysis Calculated for $C_{23}H_{29}N_2O_3Cl+1.0$ HCl+0.75 $H_2O$ (MW=466.92): C, 59.16; H, 6.80; N, 6.00; Cl, 15.19. Found: C, 59.24; H, 7.19; N, 5.95; Cl, 15.02.

EXAMPLE 31 methyl (D)-2R-[[(8-chlorodibenz[b,f][1,4] oxazepine-10(11H]-yl]carbonyl]amino]propanoate (31)

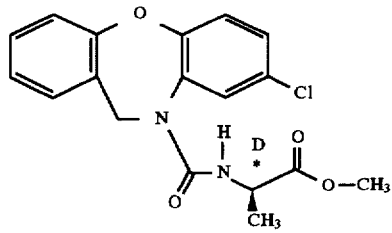

By the method described in Example 18, (D)-alaninemethylester hydrochloride (0.71 g, 5.1 mmol) in mL of $CH_2Cl_2$ with molecular sieves #3A (10 g) and NMM (1.0 g, 10.2 mmol) was reacted with the title compound of Example 2 (1.5 g, 5.1 mmol) to produce 1.7 g of the title product after HPLC purification on silica gel.

[α]$_D$–65.4° (CHCl$_3$)

Analysis Calculated for C$_{18}$H$_{17}$N$_2$O$_4$Cl+0.05 CH$_2$Cl$_2$ (MW=365.04): C, 59.39; H, 4.72; N, 7.67; Cl, 10.68. Found: C, 59.47; H, 4.84; N, 7.65; Cl, 10.73.

EXAMPLE 32 methyl (L)-2R-[[(8-chlorodibenz[b,f][1,4]oxazepine-10-(11H)-yl)carbonyl]amino]propanoate (32)

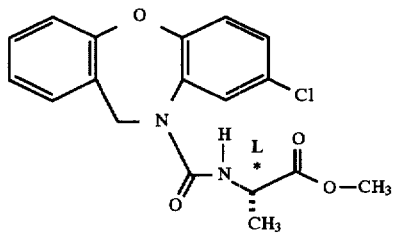

By the method described in Example 18, (L)-alanine methyl ester hydrochloride (1.2 g., 5.1 mmol) in 50 mL of CH$_2$Cl$_2$ with molecular sieves #3A (5 g) and NMM (1.4 g, 13.8 mmol) was reacted with the title compound of Example 2 (1.6 g, 5.6 mmol) to produce 1.6 g of the title product after HPLC purification on silica gel.

[α]$_D$+68.4° (CHCl$_3$)

Analysis Calculated for C$_{18}$H$_{17}$N$_2$O$_4$Cl+0.02 CH$_2$Cl$_2$ (MW=362.50): C, 59.71; H, 4.74; N, 7.73; Cl, 10.17. Found: C, 59.53; H, 4.86; N, 7.57; Cl, 10.25.

EXAMPLE 33

[D]-2R-[[8-chlorodibenz[b,f][1,4]oxazepine-10 (11H)-yl)carbonyl]amino]propanoic acid (33)

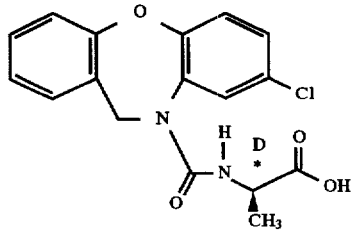

By the method described in Example 4, the title compound of Example 31 (1.2 g, 3.3 mmol) in 30 mL of THF was treated with 85% potassium hydroxide (KOH, 0.44 g, 6.6 mmol) dissolved in 45 mL of water to yield 1.1 g of the title compound.

[α]$_D$–31.2° (CHCl$_3$)

Analysis Calculated for C$_{17}$H$_{15}$N$_2$O$_4$Cl+0.625 H$_2$O+0.02 CH$_2$Cl$_2$+0.02 EtOAc (MW=361.49): C, 56.82; H, 4.59; N, 7.75; Cl, 10.20. Found: C, 56.98; H, 4.61; N, 7.31; Cl, 10.32.

EXAMPLE 34

(L)-2S-[[(8-chlorodibenz[b,f][1,4]oxazepine-10 (11H)-yl)carbonyl]amino]propanoic acid (34)

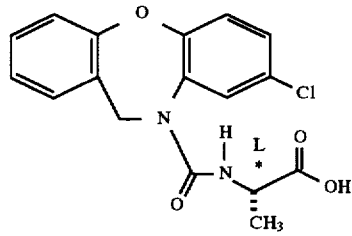

By the method described in Example 4, the title compound of Example 32 (1.3 g, 3.7. mmol) in 30 mL of THF was treated with 85% KOH (0.45 g, 7.4 mmol) dissolved in 50 mL of water to yield 1.3 g of the title compound.

[α]$_D$+25.9° (CHCl$_3$)

Analysis Calculated for C$_{17}$H$_{15}$N$_2$O$_4$Cl+0.5 H$_2$O (MW= 355.78): C, 57.39; H, 4.53; N, 7.87; Cl, 9.46. Found: C, 57.43; H, 4.58; N, 7.44; Cl, 9.99.

EXAMPLE 35

8-chloro-N-[1R-[[(4-pyridinylmethyl)amino] carbonyl]ethyl]dibenz[b,f][1,4]-oxazepine-10(11H)-carboxamide (35)

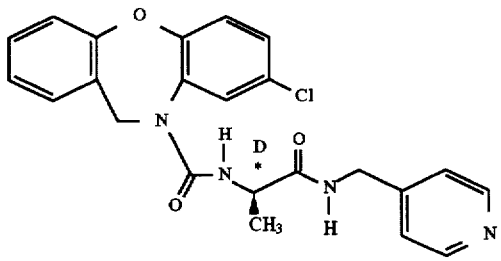

By the method described in Example 5, the title compound of Example 33 (0.53 g, 1.5 mmol) in 25 mL of CH$_2$CL$_2$ was converted to its mixed anhydride with NMM (0.15 g, 1.5 mmol) and IBCF (0.20 g, 1.5 mmol) and coupled to 4-(aminomethyl)pyridine (0.17 g, 1.5 mmol). This procedure gave 470 mg of the title compound after HPLC purification on silica gel.

[α]$_D$+150.5° (CHCl$_3$)

Analysis Calculated for C$_{23}$H$_{21}$N$_4$O$_3$Cl+0.5 H$_2$O+0.05 CH$_2$CL$_2$ (MW=450.15): C, 61.50; H, 4.95; N, 12.45; Cl, 8.66. Found: C, 61.84; H, 5.01; N, 12.75; Cl, 8.43.

EXAMPLE 36

8-chloro-N-[1R-[[(4-pyridinylmethyl)amino]carbonyl]ethyl]dibenz[b,f][1,4]oxazepine-10(11H)-carboxamide, monohydrochloride hydrate (36)

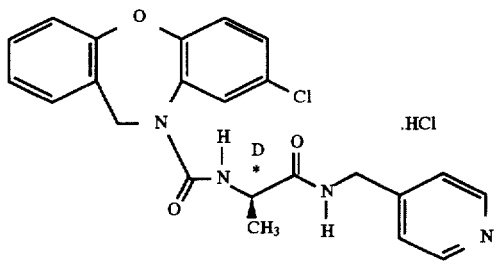

The product of Example 35 (440 mg, 1.0 mmol) was dissolved in 40 mL of water and 10 mL of 4N HCl and the resulting solution was filtered and lyophilized. The resulting foam was triturated with Et$_2$O, filtered, and dried in vacuo to provide 443 mg of the title compound.

[α]$_D$ –46.0° (MeOH)

Analysis Calculated for C$_{23}$H$_{21}$N$_4$O$_3$Cl+1.1 HCl+1.25 H$_2$O (MW=499.53): C, 55.30; H, 4.96; N, 11.22; Cl, 14.90. Found: C, 55.10; H, 4.80; N, 11.39; Cl, 14.86.

EXAMPLE 37

(L)-8-chloro-N-[1S-[[(4-pyridinylmethyl)amino]carbonyl]ethyl]dibenz[b,f][1,4]-oxazepine-10 (11H)-carboxamide (37)

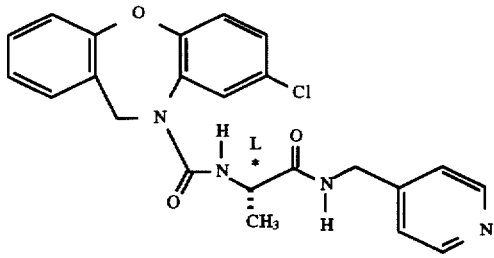

By the method described in Example 5, the title compound of Example 34 (0.53 g, 1.5 mmol) in 25 mL of CH$_2$CL$_2$ was converted to its mixed anhydride with NMM (0.15 g, 1.5 mmol) and IBCF (0.20 g, 1.5 mmol) and coupled to 4-(aminomethyl)pyridine (0.17 g, 1.5 mmol). This procedure gave 470 mg of the title compound after HPLC purification on silica gel.

[α]$_D$ –3.1° (CHCl$_3$)

Analysis Calculated for C$_{23}$H$_{21}$N$_4$O$_3$Cl+0.625 H$_2$O (MW=448.16): C, 61.64; H, 5.00; N, 12.94; Cl, 7.81. Found: C, 61.59; H, 5.18; N, 13.16; Cl, 8.03.

EXAMPLE 38

(L)-8-chloro-N-[1S-[[(4-pyridinylmethyl)amino]carbonyl]ethyl]dibenz[b,f][1,4]oxazepine-10(11H)-carboxamide, monohydrochloride (38)

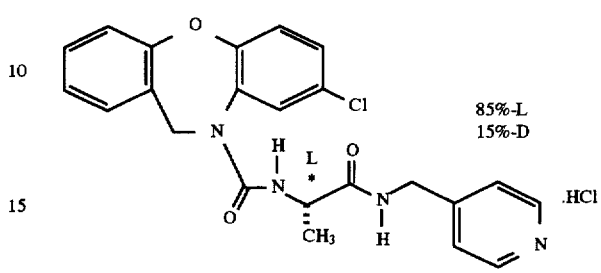

The product of Example 37 (460 mg, 1.03 mmol) was dissolved in 40 mL of Et$_2$O and 10 mL of CH$_2$Cl$_2$ and the resulting solution was treated dropwise with 6.9 HCl/dioxane until no further precipitation was noted on subsequent drops of HCl. All solvent was removed under reduced pressure to give a white solid that was triturated with Et$_2$O, filtered, washed with Et$_2$O, and dried in vacuo to provide 440 mg of the title compound.

[α]$_D$ +8.9° (CHCl$_3$)

Analysis Calculated for C$_{23}$H$_{21}$N$_4$O$_3$Cl+1.0 HCl+0.75 H$_2$O (MW=486.87): C, 56.74; H, 4.87; N, 11.51; Cl, 14.56. Found: C, 56.67; H, 4.95; N, 11.17; Cl, 14.18.

EXAMPLE 39

8-chloro-N-(4-pyridinyl)dibenz[b,f][1,4]oxazepine-10(11H)-carboxamide (39)

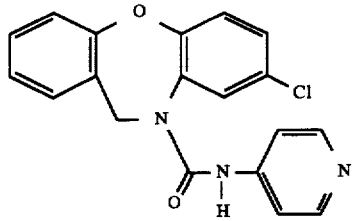

By the method described in Example 18, 4-aminopyridine (1.3 g, 14.0 mmol) in 40 mL of CH$_2$Cl$_2$ with molecular sieves #5A (5 g) and Et$_3$N (1.4 g, 15.0 mmol) was reacted with the title compound of Example 2 (4.1 g, 14.0 mmol) to produce 4.4 g of the title product after HPLC purification on silica gel.

Analysis Calculated for C$_{19}$H$_{14}$N$_3$O$_2$Cl+0.25 H$_2$O+0.1 CH$_2$CL$_2$ (MW=365.04): C, 59.39; H, 4.72; N, 7.67; Cl, 10.68. Found: C, 59.47; H, 4.84; N, 7.65; Cl, 10.73.

EXAMPLE 40

8-chloro-N-(4-pyridinyl)dibenz[b,f][1,4]oxazepine-10(11H)-carboxamide, monohydrochloride (40)

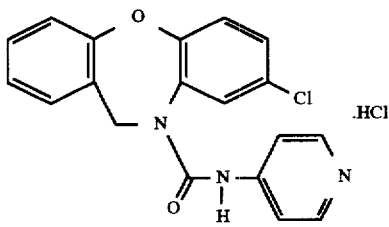

The product of Example 39 (500 mg, 1.3 mmol) was dissolved in a mixture of 50 mL of Et₂O, 5 mL of CH₂Cl₂, and 5 mL of MeOH and the resulting-solution was treated dropwise with 6.9 HCl/dioxane until no further precipitation was noted on subsequent drops of HCl. All solvent was removed under reduced pressure to give a white glass powder that was triturated with Et₂O, filtered, washed with Et₂O, and dried in vacuo to provide 464 mg of the title compound.

Analysis Calculated for $C_{19}H_{14}N_3O_2Cl+1.0$ HCl+0.66 $H_2O$ (MW=400.14): C, 57.03; H, 4.11; N, 10.50; Cl, 17.72. Found: C, 57.23; H, 4.43; N, 10.03; Cl, 18.06.

EXAMPLE 41

8-chloro-N-[1R-[[(methoxy)methylamino]-carbonyl]ethyl]dibenz[b,f][1,4]oxazeptne-10(11H)-carboxamide (41)

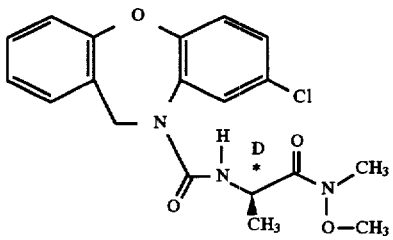

By the method described in Example 5, the title compound of Example 33 (0.45 g, 1.3 mmol) in 30 mL of CH₂Cl₂ was converted to its mixed anhydride with NMM (0.13 g, 1.3 mmol) and IBCF (0.17 g, 1.3 mmol) and coupled to N,O-dimethylhydroxylamine. HCl (0.12 g, 1.3 mmol) using 0.13 g (1.3 mmol) of NMM to absorb the additional HCl. This procedure gave 470 mg of the title compound after HPLC purification on silica gel.

Analysis Calculated for $C_{19}H_{20}N_3O_4Cl+0.125$ $H_2O$ (MW=392.09): C, 58.20; H, 5.21; N, 10.72. Found: C, 58.05; H, 5.20; N, 10.56.

EXAMPLE 42

8-chloro-N-[[[(methoxy)methylamino]carbonyl]methyl]dibenz[b,f][1,4]oxazepine-10(11H)-carboxamide (42)

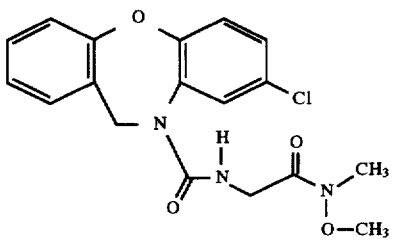

By the method described in Example 5, the title compound of Example 4 (1.2 g, 3.6 mmol) in 40 mL of THF was converted to its mixed anhydride with NMM (0.42 g, 3.6 mmol) and IBCF (0.49 g, 3.6 mmol) and coupled to N,O-dimethylhydroxylamine HCl (0.35 g, 3.6 mmol) using an additional 0.36 mmol (3.6 mmol) of NMM to liberate the free base of N,O-dimethylhydroxylamine HCl. This procedure gave 726 mg of the title compound after HPLC purification on silica gel.

Analysis Calculated for $C_{18}H_{18}N_3O_4Cl+0.02$ $CH_2Cl_2$ (MW=379.76): C, 56.99; H, 4.85; N, 11.07; Cl, 9.71. Found: C, 56.78; H, 4.74; N, 10.98; Cl, 9.96.

EXAMPLE 43 phenylmethyl 8-chlorodibenz[b,f][1,4]oxazepine-10(11H)-carboxylate (43)

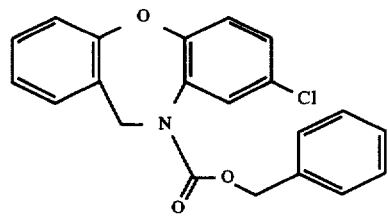

To the title product of Example I (1.0 g, 4.3 mmol) dissolved in 20 mL of THF was added 60% NaH in mineral oil dispersion (200 mg, 5.5 mmol) followed by benzylchloroformate (2 mL, 14.0 mmol). The reaction was then stirred at room temperature for 2 hours, . heated at 40° C. for 3 hours, and stirred at room temperature for 24 hours before all solvent was removed under reduced pressure. The residue was purified by silica gel chromatography to yield 1.2 g of the title material.

Analysis Calculated for $C_{21}H_{16}NO_3Cl$ (MW=365.82): C, 68.95; H, 4.41; N, 3.83. Found: C, 69.14; H, 4.63; N, 3.75.

EXAMPLE 44

(4-pyridinyl)methyl 8-chlorodibenz[b,f][1,4]-oxazepine-10(11H)-carboxylate (44)

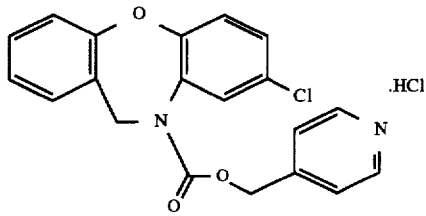

A THF (50 mL) solution of the title product of Example 1 (1.0 g, 4.3 mmol) and carbonyl diimidazole (0.98 g, 6.0 mmol) was refluxed for 17 hours, cooled to room temperature, treated with 4-pyridyl carbinol (1.0 g, 9.2 mmol), and refluxed 48 hours. All solvent was removed under reduced pressure and the residue, dissolved in DMF and combined with another 1.0 g (9.2 mmol) of 4-pyridyl carbinol, was heated at DMF reflux for 17 hours. The reaction mixture was partitioned between EtOAc and water and the organic phase was separated, washed with water and brine, dried (MgSO$_4$), and stripped of all solvent under reduced pressure. The residue oil was purified by silica gel chromatography to provide 1.0 g of the free base of the title compound. This material was dissolved in water and 1N HCl and lyophilized to give the title material.

Analysis Calculated for $C_{20}H_{15}N_2O_3Cl$+1.3 HCl+0.6 H$_2$O (MW=366.80): C, 56.51; H, 4.14; N, 6.59; Cl, 19.27. Found: C, 56.52; H, 4.18; N, 6.52; Cl, 19.27.

EXAMPLE 45

8-chloro-N-(4-pyridinylmethyl)dibenz[b,f][1,4]oxazepine-10(11H)-carboxamide, monohydrochloride (45)

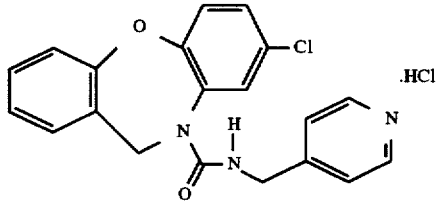

By the method described in Example 18, the title compound of Example 2 in CH$_2$Cl$_2$ with molecular sieves #5A and Et$_3$N was reacted with 4-(aminomethyl)pyridine to generate the free base of the title product. This material was converted to the title compound by the method described in Example 40.

Analysis Calculated for $C_{20}H_{16}N_3O_2Cl$+1.5 HCl+1.5 H$_2$O (MW=447.54): C, 53.68; H, 4.62; N, 9.39; Cl, 19.80. Found: C, 53.65; H, 4.32; N, 9.37; Cl, 19.55.

EXAMPLE 46

8-chloro-N-(3-pridinylmethyl)dibenz[b,f]-1,4]oxazepine-10(11H) -carboxamide, monohydrochloride (46)

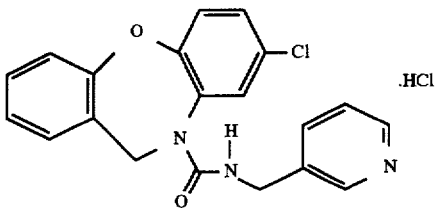

By the method described in Example 18, the title compound of Example 2 in CH$_2$Cl$_2$ with molecular sieves #5A and Et$_3$N was reacted with 3-(aminomethyl)pyridine to generate the free base of the title product. This material was converted to the title compound by the method described in Example 40.

Analysis Calculated for $C_{20}H_{16}N_3O_2Cl$+1.25 HCl+1.25 H$_2$O (MW=433.92): C, 55.36; H, 4.59; N, 9.68; Cl, 18.38. Found: C, 55.58; H, 4.37; N, 9.72; Cl, 18.87.

EXAMPLE 47

8-chloro-N-(2-pyridinylmethyl)dibenz[b,f]-1,4] oxazepine-10(11H]-carboxamide, monohydrochloride(47)

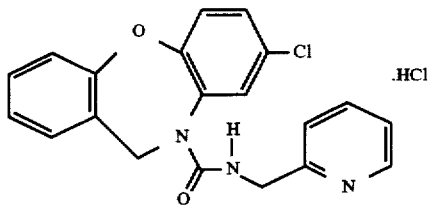

By the method described in Example 18, the title compound of Example 2 in CH$_2$Cl$_2$ with molecular sieves #5A and Et$_3$N was reacted with 2-(aminomethyl)pyridine to generate the free base of the title product. This material was converted to the title compound by the method described in Example 40.

Analysis Calculated for $C_{20}H_{16}N_3O_2Cl$+1.5 HCl+1.5 H$_2$O (MW=447.54): C, 53.68; H, 4.62; N, 9.39; Cl, 19.80. Found: C, 53.20; H, 4.17; N, 9.35; Cl, 19.45.

EXAMPLE 48

8-chloro-10,11(H)dihydrodibenzo [b,f][1,4] thiazepine (48)

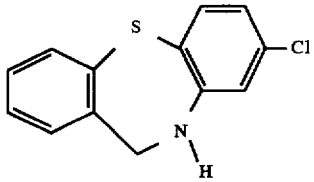

(a) 4-chloro-2-nitro-1-(phenylthio)benzene (48a)

Potassium hydroxide (6.15 g; 87%) was added to a stirred solution of thiophenol (10.0 g) in N,N-dimethylformamide (170 mL) at room-temperature. When most of the potassium hydroxide appeared to have dissolved, 2,5-dichloronitrobenzene (17.4 g) was added, and the initially dark solution turned bright yellow with some precipitate. The reaction was placed in an oil bath at 70° C. for three hours, and then evaporated in vacuo. The residue was partitioned between chloroform and 1N NaOH and the layers were separated. The aqueous layer was extracted once more with chloroform. The chloroform solutions were combined, washed with 1N NaOH, H₂O 1N HCl, H₂O and brine, dried over MgSO₄, and evaporated in vacuo. The resulting oil was treated with cyclohexane, and the product crystallized. The crystalline product was collected by filtration, washed with hexane, and dried in vacuo at 56° C. to yield 13.73 g (57%) of yellow crystals. mp: 84°–86° C.

(b) 5-chloro-2(phenylthio)benzenamine (48b)

A solution of 4-chloro-2-nitro-1-(phenylthio)-benzene (11.0 g) and Raney nickel in ethanol (3A; 9.3 mL) was reacted in a Parr Hydrogenator under hydrogen atmosphere at 5 psi and room temperature. When the theoretical amount of hydrogen uptake was reached, the reaction was filtered to remove the catalyst and evaporated in vacuo to yield 8.61 g (88%) of a light orange solid. mp: 59°–61° C.

(c) 8-chloro-10,11-dihydrodibenzo[b,f][1,4]thiazepine (48c)

To a cold (ice water bath), stirred solution of phosgene (1.93M in toluene; 55mL) under a nitrogen atmosphere was added, dropwise, a solution of 5-chloro-2-(phenylthio) benzenamine (5.00 g) in toluene (20 mL). The reaction mixture was stirred for 30 minutes in the ice bath, and was then heated on a steam bath for 30 minutes. The resulting orange solution was evaporated in vacuo to an oil (IR: weak band at approximately 2250 cm⁻¹).

The oil was taken up in bromobenzene (25 mL) and added dropwise to a stirred mixture of aluminum chloride (2.90 g) in bromobenzene (25 mL) in an oil bath at 100° C. When the addition was complete, the oil bath temperature was increased to 150° C., and the reaction was stirred for 1.5 hours. A small amount of water was then added to quench the reaction, and the mixture was evaporated in vacuo. The residue was triturated with acetone, and the solid was collected by filtration, washed with acetone followed by ether, and dried in vacuo at 110° C. for 16 hours to yield 6.99 of white solid.

The white solid (6.64 g) was suspended with stirring in anhydrous tetrahydrofuran (175 mL) under a nitrogen atmosphere in an ice-H₂O bath, and lithium aluminum hydride (1.0M in THF; 100 mL) was added dropwise, keeping the temperature below 10° C. When the addition was complete, the ice bath was removed and the reaction was stirred to room temperature (approximately 20 minutes), and then at reflux for four hours under a nitrogen atmosphere. The reaction was then cooled in an ice-H₂O bath and quenched by the successive addition of H₂O (3.8 mL), 15% NaOH (3.8 mL), and H₂O (11.4 mL) while keeping the temperature below 15° C. The resulting mixture was filtered through a filter aide and the filter cake was washed with THF. The filtrate and washes were combined and evaporated in vacuo to a yellow oil. The oil was flash chromatographed through silica gel 60 (approximately 300 mL) using chloroform. The collected product was recrystallized from cyclohexane to yield 2.37 g (42.7%) of product as white plates. mp: 125°–127° C.

EXAMPLE 49

8-chlorodibenz[b,f][1,4]thiazepine-10(11H)-carbonyl chloride (49)

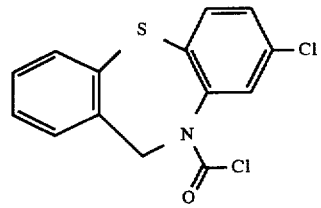

To a cold (ice-H₂O bath), stirred solution of phosgene (1.93M in toluene; 8.6 mL) in anhydrous tetrahydrofuran (40 mL) under a nitrogen atmosphere is added, dropwise, a solution of the title product of Example 48 (2.00 g) and triethylamine (1.3 mL) in anhydrous tetrahydrofuran (30 mL). The resulting mixture is stirred at room temperature for 90 minutes, and the solvent is then evaporated in vacuo to provide the title product.

EXAMPLE 50

(4-pyridinyl)methyl 8-chlorodibenzo[b,f][1,4] thiazepine-10(11H)carboxylate, 5-monohydrochloride (50)

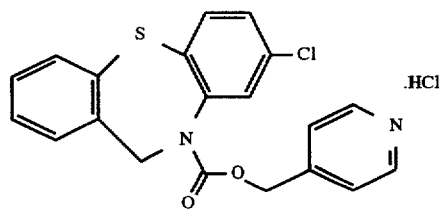

The title compound of Example 49 is reacted with 4-pyridyl carbinol (1.0 g, 9.2 mmol) by the method described in Example 44 to produce the title product HCl salt.

EXAMPLE 51

(4-pyridinyl)methyl 8-chlorodibenzo[b,f]-[1,4] thiazepine-10(11H)carboxylate, 5-oxide, monohydrochloride (51)

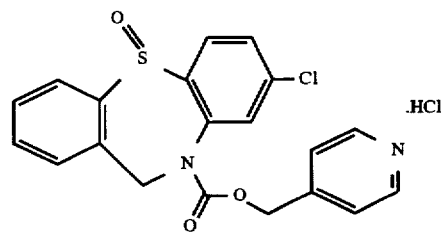

The title material is synthesized from the title material of Example 50 by treatment of this compound with 30% H₂O₂ in acetic acid at room temperature.

EXAMPLE 52

(4-pyridinyl]methyl 8-chlorodibenzo[b,f]-[1,4]
thiazepine-10(11H)-carboxylate, 5,5-dioxide,
monohydrochloride (52)

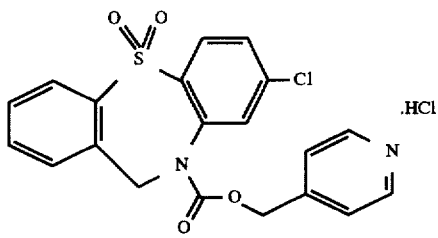

The title material is synthesized from the title product of Example 50 by treatment of this compound with 30% $H_2O_2$ in acetic acid at 50 °C.

EXAMPLE 53

8-chloro-N-[4-(4-pyridinyl]butyl]dibenzo[b,f][1,4]
thiazepine-10(11H)-carboxamide,
monohydrochloride (53)

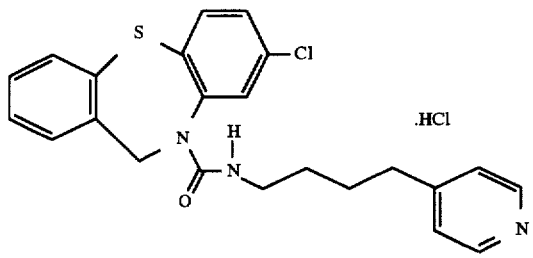

The title compound of Example 49 is reacted with the product of Example 23 by the method described in Example 18 to produce the free base of the title product. This material is converted to the title compound by the method described in Example 16.

EXAMPLE 54

8-chloro-N-[4-(4-pyridinyl)butyl]dibenzo[b,f]-[1,4]
thiazepine-10(11H)-carboxamide, 5-oxide,
monohydrochloride (54)

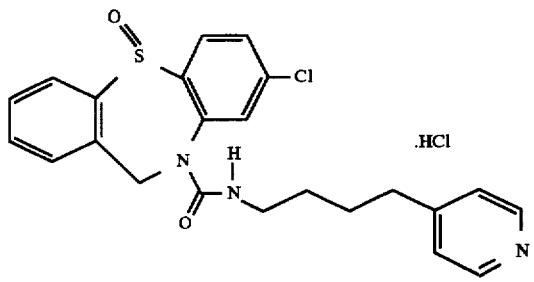

The title material is synthesized from the title material of Example 53 by treatment of this compound with 30% $H_2O_2$ in acetic acid at room temperature.

EXAMPLE 55

8-chloro-N-[4-(4-pyridinyl)butyl]dibenzo[b,f]-[1,4]
thiazepine-10(11H)-carboxamide, 5,5-dioxide,
monohydrochloride (55)

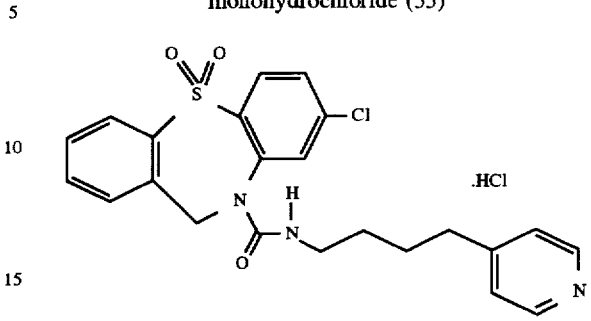

The title material is synthesized from the title product of Example 53 by treatment of this compound with 30% $H_2O_2$ in acetic acid at 50° C.

The foregoing examples are provided to enable one of ordinary skill in the art to practice the present invention. These examples are merely illustrative, however, and should not be read as limiting the scope of the invention as it is claimed in the appended claims.

(7) Description of Assays (a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., Arch. int. Pharmacodyn, 267, 131–140 (1984); C. Vander Wende et al., Fed. Proc., 15, 494 (1956); Koster et al., Fed. Proc., 18, 412 (1959); and Witken et al., J. Pharmacol. exp. Ther., 133, 400–408 (1961).]Chemicals which may be used to induce this pain include phenylbenzoquinone (PBQ) and acetic acid. As a result of the chemical irritation to the animal, a characteristic stretching and writhing of the. animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I hereinbelow.

Charles River male albino mice, weighing 20 to 30 grams, were used in this assay.

Thirty minutes after intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, are presented in Table I hereinbelow as fractions under the heading "WRITHING ASSAY." The fractions indicate the number of mice, out of ten, in which the test compound produced analgesia.

The standard initial screening dose of a test compound employed in this assay was 30 mpk per gram of body weight. If this initial screening dose of the test compound produced analgesia in seven of ten mice, then the effect of additional doses of the test compound on the writhing response was evaluated, and then the $ED_{50}$ dose was generally calculated. (The slopes of the dose-reSponse curves for all test compounds analyzed were compared as described by Tallarida and Murray, *Manual of Pharmacologic Calculations*, Page 11 (Springer Verlag, New York.

All $ED_{50}$ doses calculated are also presented hereinbelow as whole numbers in Table I under the heading "WRITHING ASSAY." As Table I shows, the most potent compound of the present invention tested in the Writhing Assay was the compound shown and discussed in Example 32. Thus, methyl (L)-2R-[[(8-chlorodibenz-[b,f][1,4]oxazepine-10-(11H)-yl)carbonyl]amino]-propanoate (Example 32) was determined to be the most potent compound of the invention tested in this assay and, thus, is the most preferred compound of the present invention. (b) prostaglandin (PGE) Antagonism Assay In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10 mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A dose ratio of $EC_{50}$ doses was then calculated from the results of each test in a manner knoWn by those of skill in the art. A test compound was determined to be "active" if the initial concentration used yielded at least a two-fold shift (dose ratio greater than or equal to 2) in the dose response curve for prostaglandin $E_2$. An estimated $pA_2$ value (a statistical constant which is a common measure of expressing the potency of a particular drug as an antagonist) was reported for "active" compounds under the assumption that the slope of the Schild plot does not deviate significantly from −1.0. If the initial concentration of test compound yielded at least a five-fold shift (dose ratio greater than or equal to 5) in the dose response curve for prostaglandin $E_2$, then varying concentrations of the test compound were assayed, and a $PA_2$ value for that compound was calculated by Schild plot calculations, as described by H. O. Schild, "pA, A New Scale for the Measurement of Drug Antagonism," Br. J. Pharmacol. 2, 189 (1947). The higher the value calculated for the $PA_2$, the more potent a particular compound is as a prostaglandin $E_2$ antagonist.

The results of this prostaglandin antagonism assay, in terms of either dose ratio or $pA_2$ value, are also presented in Table I below. The compounds of the present invention which were tested in this assay, and for which results are presented in Table I, correspond to the particular examples specified in Table I.

TABLE I

Data Generated from the Assays

| Example Number | WRITHING ASSAY Number out of Nine or Ten or $ED_{50}$ Dose (mpk) I.G. | PGE IN GUINEA PIG ILEUM $pA_2$ or Dose Ratio |
|---|---|---|
| 6 | 6/10 | 6.02 ($pA_2$) |
| 8 | 3/10 | 11.02 (dose ratio) |
| 10 | 3/10 | 2.63 (dose ratio) |
| 12 | 2/10 | * |
| 14 | 5/10 | 25.03 (dose ratio) |
| 16 | 8/10 | 1.70 (dose ratio) |
| 18 | 4/10 | 2.6 (dose ratio) |
| 20 | 2/10 | 1.80 (dose ratio) |
| 24 | 6/10 | 7.9 (dose ratio) |
| 28 | 2/10 | 2.0 (dose ratio) |
| 29 | 7/10 | Active (dose ratio) |
| 31 | 8/10 | 1.4 (dose ratio) |
| 32 | 7.2 | 3.5 (dose ratio) |
| 33 | 6/10 | 2.0 (dose ratio) |
| 34 | 2/10 | 1.7 (dose ratio) |
| 43 | * | 0.3 (dose ratio) |
| 44 | * | 365 (dose ratio) |
| 45 | 6/10 | 1.0 (dose ratio) |
| 46 | 4/10 | 2.7 (dose ratio) |
| 47 | 8/10 | * |

* = Not Tested.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound chosen from the group consisting of:

phenylmethyl N-[2-[[(8-chlorodibenz[b,f][1,4]-oxazepine-10(11H)-yl)carbonyl]amino]-2-methylpropyl]carbamate (18);

8-chloro-N-[(2H-tetrazol-5-yl)methyl]dibenz-[b,f][1,4]-oxazepine-10(11H)-carboxamide, sodium salt, hydrate (20);

8-chloro-N-[2-[[(4-pyridinyl)carbonyl]amino]-1,1-dimethylethyl]dibenz[b,f][1,4]oxazepine-10(11H) carboxamide, hydrochloride hydrate (28);

methyl (D)-2R-[[(8-chlorodibenz[b,f][1,4]oxazepine-10 (11H)-yl)carbonyl]amino]propanoate (31);

methyl (L)-2R-[[(8-chlorodibenz[b,f][1,4]oxazepine-10-(11H)-yl)carbonyl]amino]propanoate (32);

(D)-2R-[[(8-chlorodibenz[b,f][1,4]oxazepine-10(11H)-yl)carbonyl]amino]propanoic acid (33);

(L)-2S-[[(8-chlorodibenz[b,f][1,4]oxazepine-10(11H)-yl)carbonyl]amino]propanoic acid (34);

8-chloro-N-(4-pyridinyl)dibenz[b,f][1,4]oxazepine-10 (11H)-carboxamide, monohydrochloride (40); and 8-chloro-N-[1R-[[(methoxy)methylamino]-carbonyl]ethyl]-dibenz[b,f][1,4]oxazepine-10(11H)-carboxamide (41).

2. The compound of claim 1 having the structure:

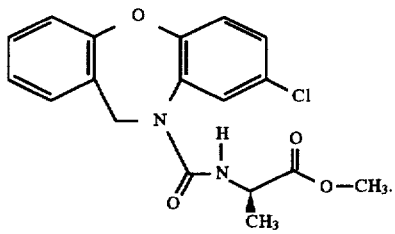

3. The compound of claim 1 having the structure:

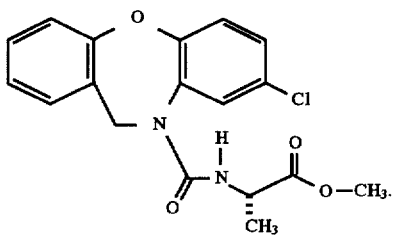

4. The compound of claim 1 having the structure:

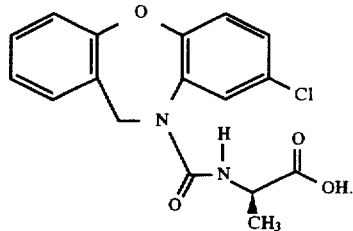

5. A pharmaceutical composition comprising a pharmaceutically-acceptable carrier and a therapeutically-effective amount of a compound chosen from the group consisting of:

phenylmethyl N-[2-[[(8-chlorodibenz[b,f][1,4]-oxazepine-10(11H)-yl)carbonyl]amino]-2-methylpropyl]carbamate (18);

8-chloro-N-[(2H-tetrazol-5-yl)methyl]dibenz-[b,f][1,4]-oxazepine-10(11H)-carboxamide,sodium salt, hydrate (20);

8-chloro-N-[2-[[(4-pyridinyl)carbonyl]amino]-1,1-dimethylethyl]dibenz[b,f][1,4]oxazepine-10(11H) carboxamide, hydrochloride hydrate (28);

methyl (D)-2R-[[(8-chlorodibenz[b,f][1,4]oxazepine-10 (11H)-yl)carbonyl]amino]propanoate (31);

methyl (L)-2R-[[(8-chlorodibenz[b,f][1,4]oxazepine-10-(11H)-yl)carbonyl]amino]propanoate (32);

(D)-2R-[[(8-chlorodibenz[b,f][1,4]oxazepine-10(11H)-yl) carbonyl]amino]propanoic acid (33);

(L)-2S-[[(8-chlorodibenz[b,f][1,4]oxazepine-10(11H)-yl) carbonyl]amino]propanoic acid (34);

8-chloro-N-(4-pyridinyl)dibenz[b,f][1,4]oxazepine-10 (11H)-carboxamide, monohydrochloride (40);

8-chloro-N-[1R-[[(methoxy)methylamino]-carbonyl]ethyl]-dibenz[b,f][1,4]oxazepine-10(11H)-carboxamide (41); and 8-chloro-N-[[[(methoxy)methylamino]carbonyl]-methyl]dibenz[b,f][1,4]oxazepine-10(11H)-carboxamide (42).

6. A method for treating pain in an animal comprising administering to said animal a therapeutically-effective amount of a compound chosen from the group consisting of:

phenylmethyl N-[2-[[(8-chlorodibenz[b,f][1,4]-oxazepine-10(11H)-yl)carbonyl]amino]-2-methylpropyl]carbamate (18);

8-chloro-N-[(2H-tetrazol-5-yl)methyl]dibenz-[b,f][1,4]-oxazepine-10(11H)-carboxamide,sodium salt, hydrate (20);

8-chloro-N-[2-[[(4-pyridinyl)carbonyl]amino]-1,1-dimethylethyl]dibenz[b,f][1,4]oxazepine-10(11H) carboxamide, hydrochloride hydrate (28);

methyl (D)-2R-[[(8-chlorodibenz[b,f][1,4]oxazepine-10 (11H)-yl)carbonyl]amino]propanoate (31);

methyl (L)-2R-[[(8-chlorodibenz[b,f][1,4]oxazepine-10-(11H)-yl)carbonyl]amino]propanoate (32);

(D)-2R-[[(8-chlorodibenz[b,f][1,4]oxazepine-10(11H)-yl) carbonyl]amino]propanoic acid (33); and (L)-2S-[[(8-chlorodibenz[b,f][1,4]oxazepine-10(11H)-yl) carbonyl]amino]propanoic acid (34).

7. The method of claim 6 wherein the compound is chosen from the group consisting of:

8-chloro-N-[2-[[(4-pyridinyl)carbonyl]amino]-1,1-dimethylethyl]dibenz[b,f][1,4]oxazepine-10(11H) carboxamide, hydrochloride hydrate (28); and methyl (L)-2R-[[(8-chlorodibenz[b,f][1,4]oxazepine-10-(11H)-yl)carbonyl]amino]propanoate (32).

* * * * *